(12) United States Patent
Cales

(10) Patent No.: US 8,489,335 B2
(45) Date of Patent: Jul. 16, 2013

(54) METHOD OF DIAGNOSING THE PRESENCE AND/OR SEVERITY OF A HEPATIC PATHOLOGY IN AN INDIVIDUAL AND/OR OF MONITORING THE EFFECTIVENESS OF A TREATMENT FOR ONE SUCH PATHOLOGY

(75) Inventor: Paul Cales, Avrille (FR)

(73) Assignees: Universite d'Angers, Angers (FR); Centre Hospitalier Universitaire D'Angers, Angers (FR)

( * ) Notice: Subject to any disclaimer, the term of this patent is extended or adjusted under 35 U.S.C. 154(b) by 982 days.

(21) Appl. No.: 11/596,486

(22) PCT Filed: May 13, 2005

(86) PCT No.: PCT/FR2005/001217
§ 371 (c)(1),
(2), (4) Date: Nov. 20, 2008

(87) PCT Pub. No.: WO2005/116901
PCT Pub. Date: Dec. 8, 2005

(65) Prior Publication Data
US 2009/0143993 A1 Jun. 4, 2009

Related U.S. Application Data

(60) Provisional application No. 60/622,886, filed on Oct. 28, 2004.

(30) Foreign Application Priority Data

May 14, 2004 (FR) ..................................... 04 05306
Oct. 28, 2004 (FR) ..................................... 04 11536

(51) Int. Cl.
*G01N 33/48* (2006.01)
(52) U.S. Cl.
USPC .......................................................... 702/19
(58) Field of Classification Search
USPC .......................................................... 702/19
See application file for complete search history.

(56) References Cited

U.S. PATENT DOCUMENTS

2003/0175686 A1* 9/2003 Rose et al. ........................ 435/5

OTHER PUBLICATIONS

The EPO international search report PCT/FR2005/001217 dated Oct. 24, 2005.
Myers R P et al: "Biochemical markers of fibrosis in patients with chronic hepatitis C: A comparison wih prothrombin time, platelet count, and age-platelet index" Digestive Diseases and Science Jan. 1, 2003 Untied States, vol. 48, No. 1, Jan. 1, 2003, pp. 146-153, XP001205546 ISSN: 0163-2116 le document en enter.
Oberti F, Valsesia E, Pilette C, Rousselet M, Bedossa P. Aube C et al, Cales P. Noninvasive diagnosis of hepatic fibrosis or cirrhosis. Gastroenterology 1997; 113: 1609-16.
Croquet V, Vuillemin E, Ternisien C, Pilette C, Oberti F, Gallois Y, Trossaert M, Rousselet MC, Chappard D, Cales P. Prothrombin index is an indirect marker of severe liver fibrosis. Eur J Gastroenterol Hepatol 2002; 14: 1133-41.
Pilette C, Cales P. Existe-t-il des marqueurs sanguins de fibrose hepatique utilisables en pratique clinique? [Do blood markers for hepatic fibrosis, that can be used in clinical practice, exist?] Rev Med Interne 2002; 23: 885-8.
Pilette C, Rousselet M, Bedossa P, Chappard D, Oberti F, Rifflet H et al, Cales P. Histopathological evaluation of liver fibrosis: quantitative image analysis vs semi-quantitative scores: comparison with serum markers. J Hepatol 1998; 28: 439-46.
Aube C, Oberti F, Korali N, Korali N, Namour A, L et al, Cales P. Ultrasonographic diagnosis of hepatic fibrosis or cirrhosis. J Hepatol 1999; 30: 472-8.
Moal F, Chappard D, Wang J, Vuillemin E, Michalak-Provost S, Rousselet MC, Oberti F, Cales P. Fractal dimension can distinguish models and pharmacological changes in liver fibrosis in rats. Hepatology 2002; 36: 840-9.
Michalak S, Rousselet MC, Bedossa P, Pilette C, Chappard D, Oberti F, Gallois Y, Cales P. Respective role of porto-septal fibrosis and centrolobular fibrosis in alcoholic liver diseases. J Pathol 2003; 201: 55-62.

* cited by examiner

*Primary Examiner* — Jerry Lin
(74) *Attorney, Agent, or Firm* — Young & Thompson

(57) ABSTRACT

The invention relates to a method of diagnosing the presence and/or severity of a hepatic pathology and/or of monitoring the effectiveness of a curative treatment against a hepatic pathology in an individual, comprising the establishment of at least one non-invasive diagnostic score, in particular a diagnostic score for portal and septal fibrosis and/or an estimate score for the fibrosis area and/or an estimate score for the fractal dimension.

11 Claims, 5 Drawing Sheets

METHOD OF DIAGNOSING THE PRESENCE AND/OR SEVERITY OF A HEPATIC PATHOLOGY IN AN INDIVIDUAL AND/OR OF MONITORING THE EFFECTIVENESS OF A TREATMENT FOR ONE SUCH PATHOLOGY

The present invention relates to the field of diagnosis in hepatology, and in particular relates to a method for the evaluation of the presence and/or severity of hepatic fibrosis of the liver, or the evaluation of the area of fibrosis, or the evaluation of the architecture of the liver (fibrosis score and fractal dimension).

For the purpose of the present invention, the term "evaluation of the presence of fibrosis" means that the question of whether or not a fibrosis exists in the patient tested by means of the method of the invention is investigated; the term "evaluation of the severity" means that a measurement of the degree of fibrosis is sought, this must be distinguished from the severity of the hepatic damage, which is a functional deficiency of the liver. The term "evaluation of the area of fibrosis" means that a measurement of the degree of liver lesion due to the fibrosis is sought. It is specified that the functional deficiency of the liver depends on the degree of anatomical lesion of the liver, but this is not a linear relationship.

The seriousness of chronic liver diseases lies in the fibrosis that is a scar secondary to the inflammation. The causes of fibrosing liver diseases are mainly B and C viral infections, alcohol and steatosis (fatty liver).

Up until now, the evaluation of the fibrosis was based on the liver needle biopsy (LNB). Liver fibrosis is classified, according to the LNB, by means of a semiquantitative fibrosis score. Several classifications exist, based on the observation of similar lesions. The description of these lesions is mainly qualitative according to a disturbance (or distortion) of the architecture of the elementary unit (at the functional and anatomical level) of the liver, namely the hepatic "lobe". The fibrosis begins at the periphery of the lobe in the "portal" space (F1 stage) so as to extend within the lobe (restricted bands of fibrosis or F2 stage) and then dissect it (extensive bands of fibrosis or F3 stage) so as to be concentric and isolate the hepatic cells (F4 stage or cirrhosis). The Métavir classification described above (Bedossa et al, 1994, Hepatology, vol. 20, pages 15-20) is one of the most commonly used. It classifies liver fibrosis into five stages from F0 to F4, the F4 stage corresponding to the ultimate stage of cirrhosis. The fibrosis is said to be clinically significant when it is at stage $F \geq 2$. The fibrosis score F is used by all liver specialists throughout the world (according to different classifications). It is the most important parameter for determining the seriousness of a liver disease, its evolutive potential and the indication for treatment. It is of determining assistance in being able to prescribe a treatment or in managing a disease. This F-score classification is semiquantitative for three reasons: a) the description of the lesions is purely qualitative and therefore evaluated by a physician who is an anatomical pathologist, b) the scoring can only be given as a finite and restricted number of stages (from 4 to 6 without counting the absence of fibrosis), c) the progression of the amount of fibrosis is not linear as a function of the stages. The quantitative aspect is due to the ordered nature of the classes according to the extension of the fibrosis within the lobe.

A purely quantitative means for measuring fibrosis exists: it is the measurement of the area (or surface) of fibrosis by means of a semiautomatic technique called image analysis. The area of fibrosis, which is compared to a panel of blood markers for fibrosis, considered as a reference, has been found to be a more reliable measurement than the Métavir score (Pilette et al, 1998, J Hepatol, vol. 28, pages 439-46).

However, LNB is an expensive and invasive examination which is therefore susceptible to complications and requires at least a day's hospitalization. The current constraints of LNB (cost, invasive procedure requiring hospitalization) limit the use thereof. Resorting to this diagnostic method remains the almost exclusive use of liver specialists. As a result, current medical management of treatment concerns patients that are often at a relatively advanced stage of the disease (cirrhosis, often complicated), for which there are fewer treatment possibilities.

Several investigations clearly demonstrate that LNB is the main limiting factor of screening and of access to treatments. The development of alternatives to LNB, which is the aim of the present invention, is part of the research recommendations of the American and French consensus conferences in 2002.

Liver fibrosis, including up to the recent cirrhosis stage, is a reversible condition. Early screening for fibrosis often makes it possible to propose steps for curing the disease or at least for limiting the consequences thereof.

The alternatives to LNB are non-invasive means, at the head of which are blood markers for fibrosis. The term "blood markers for fibrosis" in fact has two meanings. For the biologist, it involves markers that reflect one of the dynamic processes of fibrosis: fibrogenesis (production of fibrosis), fibrolysis (destruction of fibrosis). For the clinician, it involves a marker for the degree of fibrosis observed upon anatomical-pathological examination (mainly "septal" fibrosis), i.e. a static image resulting from the two dynamic processes above. In addition, the clinician differentiates these indicators into direct markers when they are derived from one of the molecules involved in the extracellular matrix (fibrosis) and into indirect markers as reflections, but not an integral part, of this visible fibrosis.

The international patent application published under the number WO 02/16949 describes a method of diagnosing inflammatory, fibrotic or cancerous diseases, in which the values of biochemical markers in the serum or the plasma of a patient are measured, said values are combined by virtue of a logistical function, and the final value of said logistical function is analyzed with a view to determining the presence of fibrosis or the presence of necrotic-inflammatory lesions in the liver. This international patent application makes it possible to propose a fibrosis test. However, the markers used are conventional biochemical markers (indirect markers) which are not specific indicators of fibrosis and can vary according to other disturbances present during liver diseases. The test marketed, corresponding to the method of patent WO 02/16949 (see also Imbert-Bismut et al, Lancet 2001, Vol. 37, pages 1069-1075), called the Fibrotest sold by the company Biopredictive, has in particular the drawback that it has difficulties in correctly classifying patients having stage F0 and F4 viral hepatitis forms.

In addition, the international patent application published under the number WO 03/073822 concerns a method for diagnosing the presence or the severity of a liver fibrosis in a patient. This method is based on the detection of three markers, namely α-2-macroglobulin, hyaluronic acid and metalloproteinase-1 tissue inhibitor.

The object of the present invention is to propose novel tools for determining the F stages of fibrosis, in particular having a score of $F \geq 2$, and for finely quantifying the exact degree of this fibrosis, with a view to diagnosing the presence and/or severity of a liver pathology and/or for monitoring the effectiveness of a curative treatment.

The monitoring of the effectiveness of a curative treatment or a treatment that suspends the disease is important. Since most chronic liver diseases are accompanied by a fibrosis, curative treatment or treatment that suspends the disease has the effect of slowing down the progression or even of causing the fibrosis to regress. It is therefore important to be able to have tests that can evaluate this variation in fibrosis.

Contrary to the tools and methods of the prior art, the present invention relates not only to fibroses for which the cause is viral, but also to fibroses for which the cause is alcoholic and to steatosis.

Furthermore, the tools of the present invention are more reliable than those of the prior art.

These tools are: (1) a diagnostic score for the presence and severity of fibrosis, also called diagnostic score of portal and septal fibrosis, (2) a noninvasive means of quantifying the area of fibrosis, and (3) a noninvasive means of determining the fractal dimension indicating the degree of distortion of the liver due to fibrosis.

The invention therefore makes it possible to determine a noninvasive diagnostic score for portal and septal fibrosis (that reflected by the Métavir score) that is clinically significant. The score according to the invention ranges from 0 (minimal fibrosis) to 1 (maximum fibrosis) with the reference threshold fixed at 0.5 for Métavir scores F≧2. This score is calculated using a subjective semiquantitative fibrosis reference: the Métavir score. The Métavir score is determined by a physician who is an anatomical pathologist, after examination of a liver fragment under the microscope. The scale of this noninvasive score is therefore virtual since it is distorted relative to the real measurement (although itself also arbitrary and subjective) of fibrosis represented by a Métavir score of 0 to 4. The scale is virtual since it is generated by a mathematical formula and there is no unit of measurement, and this scale is distorted since there is no direct (or linear) proportionality between the Métavir and noninvasive scores. However, this score of 0 to 1 represents a finer measurement of portal and septal fibrosis since it is a quantitative variable that allows finer comparisons. Two examples of a result: an individual may evolve from a score of 0.14 to 0.28 although he or she is still at the Métavir stage F0-F1 and yet has doubled his or her fibrosis score (100% progression in relative value). Conversely, when an individual evolves from a score of 0.48 to 0.52, it could be wrongly deduced that said individual has gone from a stage F0-F1 to a stage F2-F3 (or appearance of a "clinically significant" fibrosis) whereas, in reality, the progression is only 8% (in relative value—0.48 compared to 0.52 or [(0.52−0.48)/0.52]=0.08 or 8%—or 4%—0.52−0.48=0.04—in absolute value and not clinically significant.

Furthermore, the present invention makes it possible not only to determine a diagnostic score, but also to quantify the area of fibrosis of the liver. The measurement of the area of fibrosis makes it possible to obtain results that are more accurate for calculating the percentage of the liver taken up by fibrosis than the Métavir F score for fibrosis currently used. Such a quantification was not possible, up until now, in any of the methods described. It is an index (or estimate score) of the area of fibrosis ranging from 2% to 55%, respectively minimum and maximum area of fibrosis in the reference patient population. This index is calculated with a quantitative fibrosis reference. The scale of this index is therefore real since it is the direct (non distorted) reflection of an objective and non-arbitrary real measurement. It is therefore a measurement that is both precise and meaningful since it estimates without distortion a real magnitude. Two examples of results: an individual may evolve from an estimated area of fibrosis of 8.2% to 16.4%. An individual with cirrhosis may regress from 35% to 31% then 27% and, finally, 23% of estimated area of fibrosis after the cause has been interrupted or with anti-fibrosing treatment, whereas, despite a regular decrease, said patient is still at the cirrhosis stage (F4).

Furthermore, the present invention makes it possible not only to determine a diagnostic score and to quantify the area of fibrosis of the liver, but also to determine the architecture of the liver (fractal dimension). The measurement of the architecture of the liver makes it possible to obtain results that are more accurate for evaluating the degree of liver distortion due to fibrosis than the Métavir F score for fibrosis currently used. This degree of liver distortion due to fibrosis is the fractal dimension obtained by image analysis that is based on several estimating factors including the Kolmogorov dimension (Moal F et al, 2002, Hepatology, vol. 36, pages 840-9). None of the methods of the prior art makes it possible to establish a noninvasive measurement of the fractal dimension by assaying blood markers.

In fact, the inventors have developed the following scores given in table 1 below:

TABLE 1

| Aim of the test: to measure | Test name | Test acronym |
|---|---|---|
| In a chronic viral hepatitis: | | |
| The presence of clinically significant hepatic fibrosis | Noninvasive score for liver fibrosis | SNIFF |
| The area of hepatic fibrosis | Noninvasive score for the area of liver fibrosis | SNIAFF |
| The hepatic inflammatory activity | Noninvasive score for hepatic activity | SNIAH |
| In a chronic alcoholic hepatitis: | | |
| The presence of clinically significant hepatic fibrosis | Noninvasive score for liver fibrosis | SNIFFA |
| The area of hepatic fibrosis | Noninvasive score for the area of liver fibrosis | SNIAFFA |
| In a chronic hepatic steatosis: | | |
| The presence of clinically significant hepatic fibrosis | Noninvasive score for liver fibrosis | SNIFFSA |
| The area of hepatic fibrosis | Noninvasive score for the area of liver fibrosis | SNIAFFSA |
| In any individual: | | |
| The presence of clinically significant hepatic fibrosis | Noninvasive score for screening for liver fibrosis | SNIDAFF |
| In a chronic viral or alcoholic hepatitis: | | |
| The presence of clinically significant hepatic fibrosis | Noninvasive score for liver fibrosis | SNIFFAV |
| The area of hepatic fibrosis | Noninvasive score for the area of liver fibrosis | SNIAFFAV |
| The fractal dimension | Noninvasive score for the fractal dimension of liver fibrosis | SNIDIFFAV |

The diagnostic effectiveness is the percentage of individuals correctly classified compared with the LNB. The diagnostic effectiveness of the diagnostic score of the present invention increases at the extremities of the score. The SNIFF diagnostic score does not incorrectly classify any patient with viral hepatitis for F0 and F4 (and very few for F3). In other words, this SNIFF score is very effective (100% correct responses) for two essential questions posed by the clinician: is there a risk of incorrectly classifying an individual without fibrosis or an individual with cirrhosis? The diagnostic effectiveness of an SNIFF score with five variables is 90.8% for 50.0% of the patients with the lowest and the highest values. Given the errors of LNB, especially at the low (observer error) and high (sample error) stages of fibrosis, the error rate is therefore close to 0%.

The aim of the invention is therefore in particular to determine, with greater accuracy than that allowed by the tools of the prior art, whether a patient with or without known liver disease is suffering from fibrosis, and the severity of the liver damage (degree of lesion). The test according to the invention has the advantage of being able to be carried out every 6 to 12 months, whereas the LNB can only be repeated, optionally, every 3 to 5 years according to the consensus conferences.

The method according to the invention consists in combining and in measuring various direct markers for fibrosis associated with indirect markers taken in a specific combination, said markers being called variables. These variables are measured in a sample from an individual. The choice of these variables is determined by the best overall effectiveness of the combination of variables that is obtained by statistical analysis of various mathematical models, each providing a piece of information that is statistically significant and independent of the others. In other words, it involves the best effectiveness for the least number of variables. This means that any new variable in the mathematical model provides an inventive piece of information (or gain in diagnostic effectiveness) compared to a more restricted combination that might have already been the subject of a publication.

In the context of the present invention, the term "sample" is intended to mean a sample taken from an individual prior to any analysis. This sample may be a biological medium such as blood, serum, plasma, urine or saliva from said individual or one or more cells from said individual, such as a tissue biopsy, and more particularly a liver biopsy.

The term "liver pathology" is intended to mean a liver pathology chosen from chronic hepatic fibrosis of viral origin, chronic hepatic fibrosis of alcoholic origin and chronic hepatic steatosis.

In the context of the present invention, the term "individual" is intended to mean a man, a woman or an animal, young or adult, healthy or liable to be suffering from or suffering from a liver pathology such as chronic hepatic fibrosis of viral origin, chronic hepatic fibrosis of alcoholic origin or chronic hepatic steatosis, or from any other pathology, it being possible for the affected individual to be receiving or not receiving a curative treatment against this liver pathology.

The present invention therefore relates to a method of diagnosing the presence and/or severity of a liver pathology and/or of monitoring the effectiveness of a curative treatment against a liver pathology in an individual, comprising the establishment of at least one noninvasive diagnostic score, in particular of a diagnostic score for portal and septal fibrosis, and/or a noninvasive estimate score for the area of fibrosis, and/or a noninvasive estimate score for the fractal dimension, by carrying out the following steps:

a) for determining the area of fibrosis or the fractal dimension, measuring, in a sample from said individual, at least one variable chosen from the group consisting of α-2 macroglobulin (A2M), hyaluronic acid (HA or hyaluronate), apolipoprotein A1 (ApoA1), type III procollagen N-terminal propeptide (P3P), gamma-glutamyltranspeptidase (GGT), bilirubin, gamma-globulins (GLB), platelets (PLT), prothrombin time (PT), aspartate aminotransferase (ASAT), alanine aminotransferase (ALAT), urea, sodium (NA), glycemia, triglycerides, albumin (ALB), alkaline phosphatases (ALP), YKL-40 (human cartilage glycoprotein 39), tissue inhibitor of matrix metalloproteinase 1 (TIMP-1), matrix metalloproteinase 2 (MMP-2), ferritin, a') for establishing a diagnostic score for portal and septal fibrosis, measuring, in a sample from said individual, at least three variables chosen from the group consisting of α-2 macroglobulin (A2M), hyaluronic acid (HA or hyaluronate), apolipoprotein A1 (ApoA1), type III procollagen N-terminal propeptide (P3P), gamma-glutamyltranspeptidase (GGT), bilirubin, gamma-globulins (GLB), platelets (PLT), prothrombin time (PT), aspartate aminotransferase (ASAT), alanine aminotransferase (ALAT), urea, sodium (NA), glycemia, triglycerides, albumin (ALB), alkaline phosphatases (ALP), YKL-40 (human cartilage glycoprotein 39), tissue inhibitor of matrix metalloproteinase 1 (TIMP-1), matrix metalloproteinase 2 (MMP-2), ferritin; at least one of the three variables being chosen from the group consisting of platelets (PLT) and prothrombin time (PT); in the case where exactly three variables are measured, these three variables cannot together be platelets (PLT), prothrombin time (PT) and bilirubin; preferably, the at least three variables chosen do not together comprise α-2 macroglobulin (A2M), hyaluronic acid (HA or hyaluronate) and tissue inhibitor of matrix metalloproteinase 1 (TIMP-1), b) optionally, collecting at least one clinical variable characterizing said individual;

for the diagnostic score for portal and septal fibrosis, steps a') and b) above being such that at least 4 variables are measured or collected, c) combining said variables in a logistic or linear function, in order to obtain a diagnostic score for portal and septal fibrosis, and/or a diagnostic estimate score for the area of fibrosis, and/or a diagnostic estimate score for the fractal dimension;

d) diagnosing the presence and/or severity of said pathology and/or the effectiveness of said treatment based on the score obtained when performing the combining of step (c).

According to a first embodiment of the invention, in step a', the at least three variables are chosen from the group consisting of α-2 macroglobulin (A2M), apolipoprotein A1 (ApoA1), type III procollagen N-terminal propeptide (P3P), gamma-glutamyltranspeptidase (GGT), bilirubin, gamma-globulins (GLB), platelets (PLT), prothrombin time (PT), aspartate aminotransferase (ASAT), alanine aminotransferase (ALAT), urea, sodium (NA), glycemia, triglycerides, albumin (ALB), alkaline phosphatases (ALP), YKL-40 (human cartilage glycoprotein 39), tissue inhibitor of matrix metalloproteinase 1 (TIMP-1), matrix metalloproteinase 2 (MMP-2), ferritin; at least one of the three variables being chosen from the group consisting of platelets (PLT) and prothrombin time (PT); in the case where exactly three variables are measured, these three variables cannot together be platelets (PLT), prothrombin time (PT) and bilirubin; preferably, the at least three variables chosen do not together comprise α-2 macroglobulin (A2M), hyaluronic acid (HA or hyaluronate) and tissue inhibitor of matrix metalloproteinase 1 (TIMP-1).

According to a second embodiment of the invention, in step a', the at least three variables are chosen from the group consisting of α-2 macroglobulin (A2M), hyaluronic acid (HA or hyaluronate), apolipoprotein A1 (ApoA1), type III procollagen N-terminal propeptide (P3P), gamma-glutamyltranspeptidase (GGT), bilirubin, gamma-globulins (GLB), platelets (PLT), prothrombin time (PT), aspartate aminotransferase (ASAT), alanine aminotransferase (ALAT), urea, sodium (NA), glycemia, triglycerides, albumin (ALB), alkaline phosphatases (ALP), YKL-40 (human cartilage glycoprotein 39), matrix metalloproteinase 2 (MMP-2), ferritin; at least one of the three variables being chosen from the group consisting of platelets (PLT) and prothrombin time (PT); in the case where exactly three variables are measured, these three variables cannot together be platelets (PLT), prothrombin time (PT) and bilirubin; preferably, the at least three variables chosen do not together comprise α-2 macroglobulin (A2M), hyaluronic acid (HA or hyaluronate) and tissue inhibitor of matrix metalloproteinase 1 (TIMP-1).

The invention also relates to a diagnostic test for hepatic fibrosis, which implements the method of the invention. For the purpose of the present invention, the term "diagnostic" is intended to mean the establishment of the presence of a fibrosis and/or of its stage of evolution. To establish the diagnosis, the specificity of the test or of the method used is generally favored.

Advantageously, the clinical variables characterizing the individual are chosen from body weight (weight), body mass index (BMI), i.e. the weight/(size or height) 2 ratio, age (age) at the date on which the sample was collected, and cause. The term "cause" (or etiology) is intended to mean the alcoholic or viral cause. Consequently, it is clear to those skilled in the art that the "cause" clinical variable may only be used when a liver pathology such as a chronic hepatic fibrosis of viral origin or chronic hepatic fibrosis of alcoholic origin has already been diagnosed.

In the method of the invention, prior to step (c), the variables measured in step (a) or (a') and the variables collected in step (b) can be combined with one another. Consequently, it is possible to use, in the logistic function implemented in the context of the invention, either "native variables", also called "isolated or simple variables", which are variables that have not undergone any modification before introduction into the logistic function, or "combinatorial variables", which are arithmetic combinations of isolated variables with one another. By way of examples of combinatorial variables that can be used in the context of the present invention, and in a nonexhaustive manner, there are:

$GAPRI=((GGT/45)/PLT)*100$ $GLOPRI=(GLB/PLT)*100$ $GLOTRI=(GLB/PT)*100$ $HYAPRI=(HA/PLT)*100$ $HYATRI=(HA/PT)*100$ $AMPRI=(A2M/PLT)*100$ $AMTRI=(A2M/PT)*100$ $HYAMTRI=(HA*A2M)/(PT*100)$ $HYAMPRI=(HA*A2M)/(A2M*100)=HA/100$ $HAMPRI=(HA*A2M)/(PLT*100)$ $HYAMPTRI=(HA*A2M)/(PLT*PT)$ $GHAMPRI=(GLB*HA*A2M)/(PLT*1000)$ $GHAMTRI=(GLB*HA*A2M)/(PT*1000)$ $GHAMPTRI=(GLB*HA*A2M)/(PLT*PT*10)$

The acronym of these combinatorial variables uses the abbreviation of the isolated (simple) variables as a prefix and the suffix RI signifies "ratio index".

It should be noted that a different score, but similar in its principle, called APRI (=ASAT/PLT) has been published (Wai et al, Hepatology, 2003, vol 38, pages 518-526). The ASAT/ALAT ratio, hereinafter called RAT, is also part of the prior art.

According to the present invention, the name noninvasive score for liver fibrosis (acronym: SNIFF) is given to a score composed of a combination of markers, preferably blood markers, ranging from 0 to 1, estimating the score of Métavir F type for liver diseases of viral origin (SNIFF) or alcoholic origin (SNIFFA) or the two causes (SNIFFAV) or of steatotic origin (SNIFFSA). The name noninvasive score for the area of liver fibrosis (acronym: SNIAFF) is used for a score composed of a combination of markers, preferably blood markers, ranging, in the majority of cases, from 5 to 55%. It is an estimate score for the area of liver fibrosis for liver diseases of viral origin (SNIAFF) or alcoholic origin (SNIAFFA) or the two causes (SNIAFFAV) or of steatotic origin (SNIAFFSA).

The severity of a liver pathology is the evaluation of the degree of fibrosis in the liver.

In step (a') of the method of the invention, at least three variables, preferably 4, 5, 6 or 7 variables, are measured in a sample from said individual.

The measurements carried out in step (a) or (a') of the method of the invention are measurements aimed either at quantifying the variable (the case for A2M, HA, bilirubin, PLT, PT, urea, NA, glycemia, triglycerides, ALB, P3P), or at quantifying the enzymatic activity of the variable (the case for GGT, ASAT, ALAT, ALP). Those skilled in the art are aware of various direct or indirect methods for quantifying a given substance or a protein or its enzymatic activity. These methods may use one or more monoclonal or polyclonal antibodies that recognize said protein in immunoassay techniques (radioimmunoassay or RIA, ELISA assays, Western blot, etc.), the analysis of the amounts of mRNA for said protein using techniques of the Northern blot, slot blot or PCR type, techniques such as an HPLC optionally combined with mass spectrometry, etc. The abovementioned protein activity assays use assays carried out on at least one substrate specific for each of these proteins. International patent application WO 03/073822 lists methods that can be used to quantify α-2 macroglobulin (A2M) and hyaluronic acid (HA or hyaluronate).

By way of examples, and in a nonexhaustive manner, a preferred list of commercial kits or assays that can be used for the measurements carried out in step (a) or (a') of the method that is the subject of the present invention, on blood samples, is given hereinafter:

prothrombin time: the Quick time (QT) is determined by adding calcium thromboplastin (for example, Neoplastin CI plus, Diagnostica Stago, Asnières, France) to the plasma and the clotting time is measured in seconds. To obtain the prothrombin time (PT), a calibration straight line is plotted from various dilutions of a pool of normal plasmas estimated at 100%. The results obtained for the plasmas of patients are expressed as a percentage relative to the pool of normal plasmas. The upper value of the PT is not limited and may exceed 100%.

A2M: the assaying thereof is carried out by laser immunonephelometry using, for example, a Behring nephelometer analyzer. The reagent may be a rabbit antiserum against human A2M.

HA: the serum concentrations are determined with an ELISA (for example: Corgenix, Inc. Biogenic SA 34130

Mauguio France) that uses specific HA-binding proteins isolated from bovine cartilage.

P3P: the serum concentrations are determined with an RIA (for example: RIA-gnost PIIIP kit, Hoechst, Tokyo, Japan) using a murine monoclonal antibody directed against bovine skin PIIINP.

PLT: blood samples are collected in vacutainers containing EDTA (ethylenediaminetetraacetic acid) (for example, Becton Dickinson, France) and can be analyzed on an Advia 120 counter (Bayer Diagnostic).

Urea: assaying, for example, by means of a "Kinectic UV assay for urea" (Roche Diagnostics).

GGT: assaying, for example, by means of a "gamma-glutamyltransferase assay standardized against Szasz" (Roche Diagnostics).

Bilirubin: assaying, for example, by means of a "Bilirubin assay" (Jendrassik-Grof method) (Roche Diagnostics).

ALP: assaying, for example, by means of "ALP IFCC" (Roche Diagnostics).

ALAT: assaying, for example, by "ALT IFCC" (Roche Diagnostics).

ASAT: assaying, for example, by means of "AST IFCC" (Roche Diagnostics).

Sodium: assaying, for example, by means of "Sodium ion selective electrode" (Roche Diagnostics).

Glycemia: assaying, for example, by means of "glucose GOD-PAP" (Roche Diagnostics).

Triglycerides: assaying, for example, by means of "triglycerides GPO-PAP" (Roche Diagnostics).

Urea, GGT, bilirubin, alkaline phosphatases, sodium, glycemia, ALAT and ASAT can be assayed on an analyzer, for example, a Hitachi 917, Roche Diagnostics GmbH, D-68298 Mannheim, Germany.

Gamma-globulins, albumin and alpha-2 globulins: assaying on protein electrophoresis, for example: capillary electrophoresis (Capillarys), SEBIA 23, rue M Robespierre, 92130 Issy Les Moulineaux, France.

ApoA1: assaying, for example, by means of "Determination of apolipoprotein A-1" (Dade Behring) with an analyzer, for example: BN2 Dade Behring Marburg GmbH, Emil von Behring Str. 76, D-35041 Marburg, Germany.

TIMP1: assaying, for example, by means of TIMP1-ELISA, Amersham.

MMP2: assaying, for example, by means of MMP2-ELISA, Amersham.

YKL-40: assaying, for example, by means of YKL-40 Biometra, YKL-40/8020, Quidel Corporation.

PIIIP: assaying, for example, by means of PIIIP RIA kit, OCFKO7-PIIIP, cis bio international.

For the variables measured in step (a) or (a') of the method that is the subject of the present invention, the values obtained are expressed in:

mg/dl for α-2 macroglobulin (A2M),
μg/l for hyaluronic acid (HA or hyaluronate),
g/l for apolipoprotein A1 (ApoA1)**,
U/ml for type III procollagen N-terminal propeptide (P3P)**,
IU/l for gamma-glutamyltranspeptidase (GGT),
μmol/l for bilirubin,
g/l for gamma-globulins (GLB)*,
Giga/l for platelets (PLT),
% for prothrombin time (PT),
IU/l for aspartate aminotransferases (ASAT),
IU/l for alanine aminotransferases (ALAT),
mmol/l for triglycerides*,
mmol/l for urea*,
mmol/l for sodium (NA),
mmol/l for glycemia*,
g/l for albumin (ALB)*,
IU/l for alkaline phosphatases (ALP),
ng/ml for TIMP1,
ng/ml for MMP2,
ng/ml for YKL-40,
U/ml for PIIIP,
μg/l for ferritin.

The clinical variables collected in step (b) of the method that is the subject of the present invention are expressed in:
kg for body weight (weight) at the date on which the sample is collected,
years for the age (age)* at the date on which the sample is collected,
kg/m$^2$ in the BMI*: kg for the body weight, m (meter) for the body height,
code 1 for alcoholic cause and 2 for viral cause.

The variables pinpointed with an asterisk (*) are expressed with one (*) or two (**) decimals, the others are expressed without decimals.

Advantageously, the sample from the individual used in step (a) or (a') of the method that is the subject of the present invention is a biological medium such as blood, serum, plasma, urine or saliva from said individual or one or more cells from said individual, such as a tissue biopsy, and more particularly a liver biopsy. In the context of the present invention, it may be envisioned that the various variables measured in step (a) or (a') are measured in different samples from the patient. By way of examples, and in a nonexhaustive manner, one variable is measured in the urine from the individual, whereas three others are measured in the blood from the same individual, the two samples (blood and urine) being taken within a relatively short period of time. However, and particularly preferably, the sample from the individual used in step (a) or (a') of the method that is the subject of the present invention is a blood sample taken from the individual before any measurement.

According to a first embodiment of the present invention, the variables α-2 macroglobulin (A2M) and prothrombin time (PT) and at least two variables chosen from platelets (PLT), aspartate aminotransferase (ASAT), urea, hyaluronic acid (HA) and age are combined in step (c) of the method that is the subject of the present invention. Advantageously, the score obtained is a noninvasive score for liver fibrosis of viral origin, with at least four variables.

Among the preferred scores that may be obtained in this first embodiment, preference is given to the scores for which the following are combined in step (c):
α-2 macroglobulin (A2M), prothrombin time (PT), hyaluronic acid (HA) and age (score called SNIFF 4a);
α-2 macroglobulin (A2M), prothrombin time (PT), aspartate aminotransferase (ASAT) and age (score called SNIFF 4b);
α-2 macroglobulin (A2M), prothrombin time (PT), platelets (PLT), aspartate aminotransferase (ASAT) and age (score called SNIFF 5);
α-2 macroglobulin (A2M), prothrombin time (PT), platelets (PLT), aspartate aminotransferase (ASAT), urea and hyaluronic acid (HA) (score called SNIFF 6);
α-2 macroglobulin (A2M), prothrombin time (PT), platelets (PLT), aspartate aminotransferase (ASAT), urea, hyaluronic acid (HA) and age (score called SNIFF 7).

The score that may be thus obtained is a noninvasive score for liver fibrosis of viral origin called SNIFF, which gives an estimate score of 0 to 1 for the score of Métavir F type, using from 4 to 7 variables.

In a second embodiment of the present invention, in addition to the prothrombin time (PT) variable, at least three variables chosen from aspartate aminotransferase (ASAT), alanine aminotransferase (ALAT) and alkaline phosphatases (ALP), age, hyaluronic acid (HA or hyaluronate) and α-2 macroglobulin (A2M) are combined in step (c). The score that may thus be obtained is a noninvasive score for liver fibrosis of alcoholic origin called SNIFFA.

Among the preferred scores that may be obtained in this second embodiment, preference is given to the scores for which the following are combined in step (c):
  prothrombin time (PT), aspartate aminotransferase (ASAT), alanine aminotransferase (ALAT) and alkaline phosphatases (ALP) (score called SNIFFA 4b),
  prothrombin time (PT), age, hyaluronic acid (HA or hyaluronate) and α-2 macroglobulin (A2M) (score called SNIFFA 4c).

According to a third embodiment of the invention, at least the following 4 variables are combined in step (c) of the method: hyaluronic acid (HA or hyaluronate), gamma-glutamyltranspeptidase (GGT), bilirubin and platelets (PLT). The score thus obtained is a noninvasive estimate score (called SNIAFF with at least four variables) for the area of liver fibrosis ranging, in the majority of cases, from 5 to 35%. Preferably, in addition to the four variables described above, at least one, and preferably at least two variables, and even more preferably at least four variables, chosen from α-2 macroglobulin (A2M), urea, apolipoprotein A1 (ApoA1) and gamma-globulins (GLB), are combined in step (c).

Among the preferred scores that may be obtained in this third embodiment, preference is given to the scores for which the following are combined in step (c):
  hyaluronic acid (HA or hyaluronate), gamma-glutamyltranspeptidase (GGT), bilirubin, platelets (PLT) and apolipoprotein A1 (ApoA1) (score called SNIAFF 5);
  hyaluronic acid (HA or hyaluronate), gamma-glutamyltranspeptidase (GGT), bilirubin, platelets (PLT), α-2 macroglobulin (A2M) and urea (score called SNIAFF 6a);
  hyaluronic acid (HA or hyaluronate), gamma-glutamyltranspeptidase (GGT), bilirubin, platelets (PLT), urea and gamma-globulins (GLB) (score called SNIAFF 6b).

In a fourth embodiment of the present invention, a score called SNIDAFF, which is a noninvasive score for screening for liver fibrosis based on usual variables for alcoholic and viral liver pathologies, ranging from 0 to 1, can be obtained. For the purpose of the present invention, the term "screening for" should be understood to mean the search for the presence of a fibrosis regardless of its stage, either in patients with no known liver disease, or in patients with known chronic liver disease. For screening, the sensitivity of the test is a particularly important criterion.

The SNIDAFF score can advantageously be obtained by combining, in step (c) of the method of the present invention, at least the following four variables: platelets (PLT), prothrombin time (PT), aspartate aminotransferase (ASAT) and age. Preferably, in addition to the four variables described above, at least one, and preferably at least two variables, chosen from alkaline phosphatases (ALP), α-2 macroglobulin (A2M) and urea, are combined in step (c).

Thus, among the preferred scores that may be obtained in this fourth embodiment, preference is given to the scores for which the following are combined in step (c):
  platelets (PLT), prothrombin time (PT), aspartate aminotransferase (ASAT), age, alkaline phosphatases (ALP) and α-2 macroglobulin (score called SNIDAFF 6a);
  platelets (PLT), prothrombin time (PT), aspartate aminotransferase (ASAT), age, alkaline phosphatases (ALP) and urea (score called SNIDAFF 6b).

In a fifth embodiment of the present invention, a score called SNIFFSA, which is a noninvasive score for liver fibrosis for steatotic liver pathologies, ranging from 0 to 1, can be obtained. The SNIFFSA score can advantageously be obtained by combining, in step (c) of the method of the present invention, in addition to the prothrombin time (PT) variable, at least three variables chosen from aspartate aminotransferase (ASAT), triglycerides, age and glycemia.

Among the preferred scores that may be obtained in this fifth embodiment, preference is given to the scores for which the following are combined in step (c):
  prothrombin time (PT), aspartate aminotransferase (ASAT), age and glycemia (score called SNIFFSA 4a),
  prothrombin time (PT), triglycerides, age and glycemia (score called SNIFFSA 4b).

In a sixth embodiment of the present invention, the score called SNIFFAV, which is a noninvasive score for liver fibrosis for viral or alcoholic liver pathologies, ranging from 0 to 1, can be obtained. The SNIFFAV score can advantageously be obtained by combining, in step (c) of the method of the present invention, at least five of the following six variables: α-2 macroglobulin (A2M), platelets (PLT), prothrombin time (PT), urea, hyaluronic acid (HA or hyaluronate) or cause.

Among the preferred scores that may be obtained in this sixth embodiment, preference is given to the scores for which the following are combined in step (c):
  α-2 macroglobulin (A2M), platelets (PLT), prothrombin time (PT), urea and hyaluronic acid (HA or hyaluronate) (score called SNIFFAV 5);
  α-2 macroglobulin (A2M), platelets (PLT), prothrombin time (PT), urea, hyaluronic acid (HA or hyaluronate) and cause (score called SNIFFAV 6).

In a seventh embodiment of the present invention, the score called SNIAFFAV, which is a noninvasive estimate score for the area of liver fibrosis for viral or alcoholic liver pathologies ranging, in the majority of cases, from 5 to 55%, can be obtained. The SNIAFFAV score can advantageously be obtained by combining, in step (c) of the method of the present invention, in addition to the prothrombin time (PT) variable, at least three, preferably at least four, or more preferably five, six or seven variables chosen from platelets (PLT), urea, hyaluronic acid (HA or hyaluronate), bilirubin, α-2 macroglobulin (A2M), gamma-glutamyltranspeptidase (GGT), gamma-globulins (GLB), aspartate aminotransferase (ASAT) and cause.

Thus, among the preferred scores that may be obtained in this seventh embodiment, preference is given to the scores for which the following are combined in step (c):
  prothrombin time (PT), hyaluronic acid (HA or hyaluronate), bilirubin and α-2 macroglobulin (A2M) (score called SNIAFFAV 4),
  prothrombin time (PT), platelets (PLT), urea, hyaluronic acid (HA or hyaluronate) and cause (score called SNIAFFAV 5),
  prothrombin time (PT), urea, hyaluronic acid (HA or hyaluronate), bilirubin and α-2 macroglobulin (A2M) (score called SNIAFFAV 5b),
  prothrombin time (PT), hyaluronic acid (HA or hyaluronate), bilirubin, α-2 macroglublin (A2M) and cause (score called SNIAFFAV 5c),
  prothrombin time (PT), platelets (PLT), hyaluronic acid (HA or hyaluronate), bilirubin, α-2 macroglobulin (A2M), gamma-glutamyltranspeptidase (GGT), gamma-globulins (GLB) and aspartate aminotransferase (ASAT) (score called SNIAFFAV 8).

In an eighth embodiment of the present invention, the score called SNIDIFFAV, which is a noninvasive estimate score for the fractal dimension of liver fibrosis for viral or alcoholic liver pathologies ranging, in the majority of cases, from 0.7 to 1.3, can be obtained. The SNIDIFFAV score can advantageously be obtained by combining, in step (c) of the method of the present invention, at least four of the following five variables: α-2 macroglobulin (A2M), albumin (ALB), prothrombin time (PT), hyaluronic acid (HA or hyaluronate), alanine aminotransferase (ALAT), aspartate aminotransferase (ASAT) and age.

Among the preferred scores that may be obtained in this eighth embodiment, preference is given to the scores for which the following are combined in step (c):

α-2 macroglobulin (A2M), prothrombin time (PT), albumin (ALB) and age (score called SNIDIFFAV 4a), α-2 macroglobulin (A2M), prothrombin time (PT), albumin (ALB) and hyaluronic acid (HA or hyaluronate) (score called SNIDIFFAV 4b), α-2 macroglobulin (A2M), albumin (ALB), prothrombin time (PT), alanine aminotransferase (ALAT), aspartate aminotransferase (ASAT) and age (score called SNIDIFFAV 6).

In a ninth embodiment of the present invention, the score called SNIAFFA, which is a noninvasive estimate score for the area of liver fibrosis for alcoholic liver pathologies ranging, in the majority of cases, from 5 to 55%, can be obtained. The SNIAFFA score can advantageously be obtained by combining, in step (c) of the method of the present invention, in addition to the prothrombin time (PT) variable, at least three variables chosen from α-2 macroglobulin (A2M), hyaluronic acid (HA or hyaluronate), platelets (PLT) and weight of the individual.

Among the preferred scores that may be obtained in this ninth embodiment, preference is given to the scores for which the following are combined in step (c):

prothrombin time (PT), α-2 macroglobulin (A2M), hyaluronic acid (HA or hyaluronate) and weight of the individual (scores called SNIAFFA 4a and SNIAFFA 4b), prothrombin time (PT), α-2 macroglobulin (A2M), hyaluronic acid (HA or hyaluronate) and platelets (PLT) (score called SNIAFFA 4c).

In a tenth embodiment of the present invention, the score called SNIAFFSA, which is a noninvasive estimate score for the area of liver fibrosis for steatotic liver pathologies ranging, in the majority of cases, from 5 to 35%, can be obtained. The SNIAFFSA score can advantageously be obtained by combining, in step (c) of the method of the present invention, in addition to the three variables prothrombin time (PT), gamma-globulins (GLB) and weight, at least one variable, preferably at least two variables, chosen from hyaluronic acid (HA or hyaluronate), platelets (PLT), age and BMI of the individual.

Among the preferred scores that may be obtained in this tenth embodiment, preference is given to the scores for which the following are combined in step (c):

prothrombin time (PT), gamma-globulins (GLB), weight and age (score called SNIAFFSA 4), prothrombin time (PT), gamma-globulins (GLB), weight, hyaluronic acid (HA or hyaluronate), platelets (PLT) and BMI (score called SNIAFFSA 6).

As a variant, the present invention also relates to a method of diagnosing the presence and/or indicating the severity of a liver pathology and/or of monitoring the effectiveness of a curative treatment against a liver pathology in an individual, comprising the following steps:

a') measuring, in a sample from said individual, at least one variable chosen from the group consisting of α-2 macroglobulin (A2M), hyaluronic acid (HA or hyaluronate), apolipoprotein A1 (ApoA1), gamma-glutamyltranspeptidase (GGT), bilirubin, gamma-globulins (GLB), platelets (PLT), prothrombin time (PT), aspartate aminotransferase (ASAT), alanine aminotransferase (ALAT), urea, sodium (NA), triglycerides, glycemia, albumin (ALB) and alkaline phosphatases (ALP), YKL-40 (human cartilage glycoprotein 39), tissue inhibitor of matrix metalloproteinase 1 (TIMP-1), matrix metalloproteinase 2 (MMP-2), ferritin;

b') optionally, collecting at least one clinical variable characterizing said individual;

c') combining, in a logistic or linear function, the variable(s) measured in (a') and, optionally, the variables collected in (b'), in order to obtain a score;

d') diagnosing the presence and/or severity of said pathology based on the score obtained when performing the combining of step (c').

The characteristics of steps (a), (b), (c) and (d) described above (sample, assaying of variables, unit of variables) apply mutatis mutandis to steps (a'), (b'), (c') and (d').

According to a first embodiment of this variant of the invention, the following two variables: α-2 macroglobulin (A2M) and hyaluronic acid (HA or hyaluronate) can be measured in step (a') so as to obtain the score called SNIAFFA 2, which is a noninvasive estimate score for the area of liver fibrosis for alcoholic liver pathologies ranging, in the majority of cases, from 5 to 55%.

It is possible to combine, with these two variables, at least one, and preferably at least two variables chosen from the weight of the individual and type III procollagen N-terminal propeptide (P3P).

Among the preferred scores that may be obtained in the first embodiment of this variant of the invention, preference is given to the scores for which the following are combined in step (c):

α-2 macroglobulin (A2M), hyaluronic acid (HA or hyaluronate) and weight of the individual, thus making it possible to obtain the SNIAFFA 3 score based on three variables, α-2 macroglobulin (A2M), hyaluronic acid (HA or hyaluronate), weight of the individual and type III procollagen N-terminal propeptide (P3P) (score called SNIAFFA 4).

According to a second embodiment of this variant of the invention, the alanine aminotransferase (ALAT) variable can be measured in step (a') of the method of the invention so as to obtain the score called SNIAH, which is a noninvasive estimate score for the necrotic-inflammatory activity of the liver for viral liver pathologies.

According to a third embodiment of this variant of the invention, the following three biological variables are measured in step (a') of the invention: prothrombin time (PT), alanine aminotransferase (ALAT) and alkaline phosphatases (ALP). These three variables combined together in step (c') of the present invention make it possible to obtain the SNIFFA 3 score (a non-invasive score for liver fibrosis of alcoholic origin, with three variables).

In addition, alternatively, noninvasive scores for liver fibrosis of alcoholic origin, called SNIFFA, using four variables can be used. Thus, the SNIFFA 4 score using four variables is determined by combining, in step (c'), the following variables: α-2 macroglobulin (A2M), age, hyaluronic acid (HA or hyaluronate) and alanine aminotransferase (ALAT), making it possible to obtain the SNIFFA 4a score.

The SNIFF, SNIFFA, SNIFFSA, SNIAH, SNIDAFF and SNIFFAV scores (or dependent variable) are predicted by a combination of biological or clinical markers (or independent variables). These combinations (or models) have been obtained by the statistical method called binary logistic regression with the following procedure:

Firstly, the independent variables were tested by univariable analysis.

Secondly, the independent variables that were significant in univariable analysis were tested in multivariable analysis by binary logistic regression with ascending or descending step by step selection.

The logistic regression produces the formula for each score in the form:

$$score = a_0 + a_1 x_1 + a_2 x_2 + \ldots$$

where the coefficients $a_i$ are constants and the variables $x_i$ are the independent variables.

This score corresponds to the logic of p where p is the probability of existence of a clinically significant fibrosis. This probability p is calculated with the following formula:

$$p = \exp(a_0 + a_1 x_1 + a_2 x_2 + \ldots)/(1 + \exp(a_0 + a_1 x_1 + a_2 x_2 + \ldots))$$

$$\text{or } p = 1/(1 + \exp(-a_0 - a_1 x_1 - a_2 x_2 - \ldots))$$

where the coefficients $a_i$ and the variables $x_i$ correspond to those of the formula for the score. The existence of a lesion (for example, clinically significant fibrosis) is determined by a probability $p > 0.5$ (unless otherwise specified). It should be noted that the terms logistic regression "score" and SNIFF "score" do not correspond to the same term of the above equations. In clinical application, SNIFF corresponds to p.

We give below the tables for each SNIFF score with, in the first column, the name of each independent variable, in the second column, the value of the associated coefficient $a_i$ (called $\beta$ in the text below and often in the literature and B in the tables below), and then its standard deviation (called S.D in the tables below) then its degree of significance (called signif in the tables below), and the last two columns give the $\exp(a_i)$ confidence interval, i.e. the confidence interval (called CI in the tables below) of the corresponding odds-ratio (called $\exp(\beta)$ in the tables).

For each SNIFF score, as defined in the variants of the invention above, the overall predictive value of the model is reflected by the "overall percentage" of individuals correctly classified in a second table.

For each score, in the applicable equation, the coefficient $\beta_i$ of each independent variable $x_i$ can vary from the value $\beta$ given in the table corresponding to said score $\pm 3.3$ standard deviations, a value also given in the tables. Similarly, $a_0$ can vary from the value of the constant given in the table $\pm 3.3$ standard deviations.

By way of example and on the basis of the tables hereinafter, those skilled in the art wishing to use the SNIFF 4a score with 4 markers will employ the following formula:

$$p = 1/(1 + \exp(-a_0 - a_1(HA \text{ in } \mu g/l) - a_2(PT \text{ in } \%) - a_3(A2M \text{ in } mg/dl) - a_4(AGE \text{ in years}))) \text{ with}$$

$a_0$ between $-3.130$ and $7.860$ ($2.365 \pm 3.3 \times 1.665$) and, preferably, $a_0$ is $2.365$, $a_1$ between $-0.002$ and $0.024$ ($0.011 \pm 3.3 \times 0.004$) and, preferably, $a_1$ is $0.011$, $a_2$ between $-0.118$ and $-0.006$ ($-0.062 \pm 3.3 \times 0.017$) and, preferably, $a_2$ is $-0.062$, $a_3$ between $0.003$ and $0.009$ ($0.006 \pm 3.3 \times 0.001$) and, preferably, $a_3$ is $0.006$, $a_4$ between $-0.016$ and $0.076$ ($0.030 \pm 3.3 \times 0.014$) and, preferably, $a_4$ is $0.030$.

The SNIFF score is expressed in gross form (all the individuals are included) or in optimized form, and in this case, the extreme individuals, characterized by a studentized residue greater than 3, are discarded from the analysis. They are always low in number, as a rule $\leq 5\%$. For this reason, among the tables provided hereinafter, some indicated with a "o", for instance SNIFF 4ao, provide $\beta$ coefficients obtained after this optimization.

In addition, those skilled in the art wishing to use scores in the context of the present invention for which the various constants $a_0$ and $a_i$ have not been provided in the present invention are capable of determining said constants. It is then necessary to have a database containing the independent variables used (as measured in step a and b) and a population of individuals having the pathology studied (alcohol and/or virus or steatosis), ideally several hundred individuals, and then to calculate the coefficients $a_i$ (or $\beta$) as indicated in step c and as explained above. The dependent variable is the lesion being sought, for example a clinically significant fibrosis defined by a Métavir score $\geq 2$.

1. For SNIFF 4a (3 markers for fibrosis + age):

| Variable | B | S.D. | Signif. | Exp (B) | CI for Exp (B) 95.0% | |
|---|---|---|---|---|---|---|
| | | | | | Lower | Upper |
| HA | 0.011 | 0.004 | 0.004 | 1.011 | 1.003 | 1.018 |
| PT | −0.062 | 0.017 | 0 | 0.94 | 0.91 | 0.971 |
| A2M | 0.006 | 0.001 | 0 | 1.006 | 1.003 | 1.009 |
| AGE | 0.03 | 0.014 | 0.028 | 1.03 | 1.003 | 1.058 |
| Constant | 2.365 | 1.665 | 0.156 | 10.641 | | |

| | Observed | | Predicted | | Correct percentage |
|---|---|---|---|---|---|
| | | | F0 + 1 vs 2-4 | | |
| | | | .00 | 1.00 | |
| Stage 4 | F0 + 1 vs 2-4 | .00 | 107 | 27 | 79.9 |
| | | 1.00 | 37 | 127 | 77.4 |
| | Overall percentage | | | | 78.5 |

Classification table. The caesura value is .500

2. For SNIFF 4ao (3 markers for fibrosis + age):

| | B | S.D. | Signif. | Exp (B) | CI for Exp (B) 95.0% | |
|---|---|---|---|---|---|---|
| | | | | | Lower | Upper |
| HA | .011 | .004 | .007 | 1.011 | 1.003 | 1.020 |
| PT | −.084 | .019 | .000 | .919 | .886 | .955 |
| A2M | .008 | .002 | .000 | 1.009 | 1.005 | 1.012 |
| AGE | .046 | .015 | .002 | 1.047 | 1.017 | 1.078 |
| Constant | 3.232 | 1.843 | .080 | 25.334 | | |

| | Observed | | Predicted | | Correct percentage |
|---|---|---|---|---|---|
| | | | F0 + 1 vs 2-4 | | |
| | | | .00 | 1.00 | |
| Stage | F0 + 1 vs 2-4 | .00 | 105 | 25 | 80.8 |
| | | 1.00 | 35 | 127 | 78.4 |
| | Overall percentage | | | | 79.5 |

Classification table. The caesura value is .500

3. For SNIFF 4b with 3 markers for fibrosis + age:

|  | B | S.D. | Signif. | Exp (B) | CI for Exp (B) 95.0% | |
|---|---|---|---|---|---|---|
|  |  |  |  |  | Lower | Upper |
| PT | −0.67 | .016 | .000 | .936 | .906 | .966 |
| A2M | .005 | .002 | .001 | 1.005 | 1.002 | 1.008 |
| AGE | .049 | .013 | .000 | 1.050 | 1.023 | 1.077 |
| ASAT | .018 | .005 | .000 | 1.019 | 1.009 | 1.028 |
| Constant | 2.024 | 1.647 | .219 | 7.567 |  |  |

Classification table (a)

|  |  |  | Predicted | | Correct |
|---|---|---|---|---|---|
|  |  |  | F0 + 1 vs 2-4 | | |
|  | Observed |  | .00 | 1.00 | percentage |
| Stage 4 | F0 + 1 vs 2-4 | .00 | 106 | 29 | 78.5 |
|  |  | 1.00 | 39 | 132 | 77.2 |
|  | Overall percentage |  |  |  | 77.8 |

(a) The caesura value is .500

4. For SNIFF 4bo with 3 markers for fibrosis + age:

|  | B | S.D. | Signif. | Exp (B) | CI for Exp (B) 95.0% | |
|---|---|---|---|---|---|---|
|  |  |  |  |  | Lower | Upper |
| PT | −.091 | .020 | .000 | .913 | .878 | .949 |
| ASAT | .023 | .006 | .000 | 1.023 | 1.012 | 1.035 |
| A2M | .008 | .002 | .000 | 1.008 | 1.005 | 1.012 |
| AGE | .072 | .015 | .000 | 1.074 | 1.042 | 1.107 |
| Constant | 2.412 | 1.902 | .205 | 11.154 |  |  |

|  |  |  | Predicted | | Correct |
|---|---|---|---|---|---|
|  |  |  | F0 + 1 vs 2-4 | | |
|  | Observed |  | .00 | 1.00 | percentage |
|  | F0 + 1 vs 2-4 | .00 | 102 | 26 | 79.7 |
|  |  | 1.00 | 36 | 134 | 78.8 |
|  | Overall percentage |  |  |  | 79.2 |

Classification table. The caesura value is .500.

5. For SNIFF 5 with 4 markers for fibrosis + age:

|  | B | S.D. | Signif. | Exp (B) | CI for Exp (B) 95.0% | |
|---|---|---|---|---|---|---|
|  |  |  |  |  | Lower | Upper |
| PLATELETS | −.007 | .002 | .002 | .993 | .988 | .997 |
| PT | −.059 | .017 | .000 | .943 | .912 | .975 |
| ASAT | .015 | .005 | .002 | 1.015 | 1.005 | 1.025 |
| A2M | .005 | .002 | .001 | 1.005 | 1.002 | 1.009 |
| AGE | .040 | .013 | .003 | 1.041 | 1.014 | 1.069 |
| Constant | 3.285 | 1.736 | .058 | 26.707 |  |  |

Classification table (a)

|  |  |  | Predicted | | Correct |
|---|---|---|---|---|---|
|  |  |  | F0 + 1 vs 2-4 | | |
|  | Observed |  | .00 | 1.00 | percentage |
| Stage 5 | F0 + 1 vs 2-4 | .00 | 110 | 23 | 82.7 |
|  |  | 1.00 | 36 | 135 | 78.9 |
|  | Overall percentage |  |  |  | 80.6 |

(a) The caesura value is .500

6. For SNIFF 5O with 4 markers for fibrosis + age:

|  | B | S.D. | Signif. | Exp (B) | CI for Exp (B) 95.0% | |
|---|---|---|---|---|---|---|
|  |  |  |  |  | Lower | Upper |
| PT | −.082 | .020 | .000 | .921 | .885 | .959 |
| A2M | .009 | .002 | .000 | 1.009 | 1.005 | 1.013 |
| AGE | .058 | .015 | .000 | 1.059 | 1.028 | 1.092 |
| PLT | −.008 | .003 | .002 | .992 | .986 | .997 |
| ASAT | .020 | .006 | .001 | 1.020 | 1.009 | 1.032 |
| Constant | 4.034 | 2.004 | .044 | 56.508 |  |  |

|  |  |  | Predicted | | Correct |
|---|---|---|---|---|---|
|  |  |  | F0 + 1 vs 2-4 | | |
|  | Observed |  | .00 | 1.00 | percentage |
|  | F0 + 1 vs 2-4 | .00 | 102 | 25 | 80.3 |
|  |  | 1.00 | 32 | 138 | 81.2 |
|  | Overall percentage |  |  |  | 80.8 |

Classification table. The caesura value is .500.

7. For SNIFF 6 with 5 + 1 markers for fibrosis:

|  | B | S.D. | Signif. | Exp (B) | CI for Exp (B) 95.0% | |
|---|---|---|---|---|---|---|
|  |  |  |  |  | Lower | Upper |
| PLATELETS | −.008 | .002 | .001 | .992 | .987 | .996 |
| ASAT | .010 | .005 | .038 | 1.010 | 1.001 | 1.020 |
| UREA | −.266 | .084 | .002 | .767 | .650 | .904 |
| HYALU | .023 | .006 | .000 | 1.023 | 1.011 | 1.035 |
| AMTRI | .006 | .001 | .000 | 1.006 | 1.003 | 1.009 |
| Constant | .050 | .774 | .948 | 1.052 |  |  |

With AMTRI: (A2M/PT) × 100

Classification table (a)

|  |  |  | Predicted | | Correct |
|---|---|---|---|---|---|
|  |  |  | F0 + 1 vs 2-4 | | |
|  | Observed |  | .00 | 1.00 | percentage |
| Stage 5 | F0 + 1 vs 2-4 | .00 | 110 | 22 | 83.3 |
|  |  | 1.00 | 35 | 130 | 78.8 |
|  | Overall percentage |  |  |  | 80.8 |

(a) The caesura value is .500

8. For SNIFF 6o optimized, with 5 + 1 markers for fibrosis: Variables in the equation

|  |  | B | S.D. | Wald | ddl | Signif. | Exp (B) |
|---|---|---|---|---|---|---|---|
| Stage | PLATELETS | −.010 | .003 | 12.743 | 1 | .000 | .990 |
|  | ASAT | .011 | .005 | 4.295 | 1 | .038 | 1.011 |
|  | UREA | −.365 | .096 | 14.434 | 1 | .000 | .694 |
|  | HA | .037 | .009 | 18.482 | 1 | .000 | 1.038 |
|  | AMTRI | .007 | .002 | 21.531 | 1 | .000 | 1.007 |
|  | Constant | .171 | .881 | .038 | 1 | .846 | 1.187 |

Classification table (a)

|  |  |  | Predicted | | Correct |
|---|---|---|---|---|---|
|  |  |  | F0 + 1 vs 2-4 | | |
|  | Observed |  | .00 | 1.00 | percentage |
| Stage | F0 + 1 vs 2-4 | .00 | 106 | 22 | 82.8 |
|  |  | 1.00 | 30 | 135 | 81.8 |
|  | Overall percentage |  |  |  | 82.3 |

(a) The caesura value is .500
With AMTRI: (A2M/PT) × 100

9. For SNIFF 6 with 7 markers for fibrosis + age:

|  | B | S.D. | Signif. | Exp (B) | CI for Exp (B) 95.0% | |
|---|---|---|---|---|---|---|
|  |  |  |  |  | Lower | Upper |
| PLATELETS | −.007 | .003 | .004 | .993 | .988 | .998 |
| ASAT | .012 | .005 | .021 | 1.012 | 1.002 | 1.022 |
| UREA | −.270 | .088 | .002 | .764 | .643 | .907 |
| HYALU | .021 | .006 | .001 | 1.021 | 1.009 | 1.033 |
| PT | −.049 | .018 | .007 | .952 | .919 | .987 |
| A2M | .005 | .002 | .003 | 1.005 | 1.002 | 1.008 |
| AGE | .027 | .015 | .063 | 1.028 | .998 | 1.058 |
| Constant | 3.718 | 1.929 | .054 | 41.173 |  |  |

Classification table (a)

|  |  |  | Predicted | | Correct |
|---|---|---|---|---|---|
|  |  |  | F0 + 1 vs 2-4 | | |
|  | Observed |  | .00 | 1.00 | percentage |
| Stage 7 | F0 + 1 vs 2-4 | .00 | 111 | 21 | 84.1 |
|  |  | 1.00 | 32 | 132 | 80.5 |
|  | Overall percentage |  |  |  | 82.1 |

(a) The caesura value is .500

SNIFF 7a variant with different caesura for eliminating the Metavir F3 false negatives, the β coefficients are unchanged.

|  |  |  | Predicted | | Correct |
|---|---|---|---|---|---|
|  |  |  | F0 + 1 vs 2-4 | | |
|  | Observed |  | .00 | 1.00 | percentage |
| F0 + 1 vs 2-4 |  | .00 | 90 | 42 | 68.2 |
|  |  | 1.00 | 19 | 145 | 88.4 |
| Overall percentage |  |  |  |  | 79.4 |

The caesura value is .370

10. For SNIFF 7o optimized, with 6 markers for fibrosis + age:

|  | B | S.D. | Signif. | Exp (B) | CI for Exp (B) 95.0% | |
|---|---|---|---|---|---|---|
|  |  |  |  |  | Lower | Upper |
| PLATELETS | −.010 | .003 | .001 | .990 | .984 | .996 |
| ASAT | .014 | .006 | .009 | 1.015 | 1.004 | 1.026 |
| UREA | −.401 | .105 | .000 | .669 | .544 | .823 |
| HYALU | .038 | .009 | .000 | 1.039 | 1.020 | 1.058 |
| PT | −.062 | .021 | .003 | .940 | .902 | .979 |
| A2M | .006 | .002 | .002 | 1.006 | 1.002 | 1.009 |
| AGE | .042 | .017 | .012 | 1.043 | 1.009 | 1.078 |
| Constant | 4.873 | 2.214 | .028 | 130.764 |  |  |

Classification table (a)

|  |  |  | Predicted | | Correct |
|---|---|---|---|---|---|
|  |  |  | F0 + 1 vs 2-4 | | |
|  | Observed |  | .00 | 1.00 | percentage |
| Stage 7 | F0 + 1 vs 2-4 | .00 | 108 | 20 | 84.4 |
|  |  | 1.00 | 29 | 133 | 82.1 |
|  | Overall percentage |  |  |  | 83.1 |

(a) The caesura value is .500

Optimized SNIFF 7bo variant with different caesura so as to eliminate the Métavir F3 false negatives, the β coefficients are unchanged.

|  |  | Predicted | | Correct |
|---|---|---|---|---|
|  |  | F0 + 1 vs 2-4 | | |
| Observed |  | .00 | 1.00 | percentage |
| F0 + 1 vs 2-4 | .00 | 86 | 42 | 67.2 |
|  | 1.00 | 15 | 147 | 90.7 |
| Overall percentage |  |  |  | 80.3 |

The caesura value is .290

11. For SNIFFA 3 with 3 markers for fibrosis:

|  | B | S.D. | Signif. | Exp (B) | CI for Exp (B) 95.0% | |
|---|---|---|---|---|---|---|
|  |  |  |  |  | Lower | Upper |
| PT | −.161 | .047 | .001 | .851 | .776 | .934 |
| ALAT | −.020 | .009 | .031 | .980 | .963 | .998 |
| ALP | .030 | .011 | .007 | 1.031 | 1.008 | 1.054 |
| Constant | 13.510 | 4.556 | .003 | 736506.803 |  |  |

Classification table (a)

|  |  | Predicted | | Correct |
|---|---|---|---|---|
|  |  | F0 + 1 vs 2-4 | | |
| Observed |  | .00 | 1.00 | percentage |
| F0 + 1 vs 2-4 | .00 | 24 | 5 | 82.8 |
|  | 1.00 | 8 | 57 | 87.7 |
| Overall percentage |  |  |  | 86.2 |

(a) The caesura value is .500

12. For SNIFFA 3o with 3 markers for fibrosis:

| | B | S.D. | Signif. | Exp (B) | CI for Exp (B) 95.0% Lower | Upper |
|---|---|---|---|---|---|---|
| PT | −.301 | .095 | .002 | .740 | .614 | .892 |
| ALAT | −.036 | .013 | .007 | .965 | .940 | .990 |
| ALP | .040 | .016 | .010 | 1.041 | 1.010 | 1.073 |
| Constant | 27.447 | 9.265 | .003 | 831966014903.050 | | |

Classification table (a)

| | | Predicted | | |
|---|---|---|---|---|
| | | F0 + 1 vs 2-4 | | Correct |
| Observed | | .00 | 1.00 | percentage |
| F0 + 1 vs 2-4 | .00 | 23 | 3 | 88.5 |
| | 1.00 | 4 | 61 | 93.8 |
| Overall percentage | | | | 92.3 |

(a) The caesura value is .500

13. For SNIFFA 4a with 3 markers for fibrosis + age:

| | B | S.D. | Signif. | Exp (B) | CI for Exp (B) 95.0% Lower | Upper |
|---|---|---|---|---|---|---|
| AGE | −.099 | .049 | .042 | .906 | .823 | .996 |
| ALAT | −.032 | .015 | .027 | .968 | .941 | .996 |
| HYALU | .036 | .013 | .007 | 1.036 | 1.010 | 1.064 |
| A2M | .019 | .008 | .017 | 1.019 | 1.003 | 1.035 |
| Constant | −.310 | 2.437 | .899 | .734 | | |

Classification table (a)

| | | | Predicted | | |
|---|---|---|---|---|---|
| | | | F0 + 1 vs 2-4 | | Correct |
| | Observed | | .00 | 1.00 | percentage |
| Stage 1 | F0 + 1 vs 2-4 | .00 | 23 | 4 | 85.2 |
| | | 1.00 | .7 | 54 | 88.5 |
| | Overall percentage | | | | 87.5 |

(a) The caesura value is .500

14. For SNIFFA 4ao with 3 markers for fibrosis + age: Variables in the equation

| | B | S.D. | Wald | ddl | Signif. | Exp (B) | CI for Exp (B) 95.0% Lower | Upper |
|---|---|---|---|---|---|---|---|---|
| ALAT | −.042 | .017 | 6.092 | 1 | .014 | .959 | .927 | .991 |
| HA | .034 | .012 | 7.694 | 1 | .006 | 1.034 | 1.010 | 1.059 |
| A2M | .029 | .012 | 6.400 | 1 | .011 | 1.030 | 1.007 | 1.053 |
| AGE | −.176 | .072 | 5.968 | 1 | .015 | .838 | .728 | .966 |
| Constant | 1.038 | 2.549 | .166 | 1 | .684 | 2.825 | | |

14. For SNIFFA 4ao with 3 markers for fibrosis + age: Variables in the equation -continued Classification table (a)

| | | | Predicted | | |
|---|---|---|---|---|---|
| | | | F0 + 1 vs 2-4 | | Correct |
| | Observed | | .00 | 1.00 | percentage |
| Stage | F0 + 1 vs 2-4 | .00 | 24 | 3 | 88.9 |
| | | 1.00 | 4 | 55 | 93.2 |
| | Overall percentage | | | | 91.9 |

(a) The caesura value is .500

15. For SNIFFA 4b with 4 markers for fibrosis:

| | B | S.D. | Signif. | Exp (B) | CI for Exp (B) 95.0% Lower | Upper |
|---|---|---|---|---|---|---|
| PT | −.187 | .054 | .001 | .830 | .746 | .923 |
| ALAT | −.026 | .010 | .012 | .974 | .955 | .994 |
| ALP | .036 | .012 | .004 | 1.036 | 1.012 | 1.061 |
| RAT | −.739 | .427 | .083 | .477 | .207 | 1.103 |
| Constant | 16.629 | 5.327 | .002 | 16674698.481 | | |

Classification table (a)

| | | Predicted | | |
|---|---|---|---|---|
| | | F0 + 1 vs 2-4 | | Correct |
| Observed | | .00 | 1.00 | percentage |
| F0 + 1 vs 2-4 | .00 | 25 | 4 | 86.2 |
| | 1.00 | 7 | 58 | 89.2 |
| Overall percentage | | | | 88.3 |

(a) The caesura value is .500
With RAT = ASAT/ALAT

16. For SNIFFA 4bo with 4 markers for fibrosis:

| | B | S.D. | Signif. | Exp (B) | CI for Exp (B) 95.0% | |
|---|---|---|---|---|---|---|
| | | | | | Lower | Upper |
| PT | −.435 | .165 | .008 | .648 | .469 | .894 |
| ALAT | −.058 | .023 | .012 | .944 | .902 | .988 |
| ALP | .088 | .033 | .007 | 1.092 | 1.025 | 1.164 |
| RAT | −1.958 | .818 | .017 | .141 | .028 | .701 |
| Constant | 39.515 | 15.768 | .012 | 1449620822354434400.000 | | |

Classification table (a)

| | | Predicted | | |
|---|---|---|---|---|
| | | F0 + 1 vs 2-4 | | Correct |
| Observed | | .00 | 1.00 | percentage |
| F0 + 1 vs 2-4 | .00 | 23 | 2 | 92.0 |
| | 1.00 | 4 | 59 | 93.7 |
| Overall percentage | | | | 93.2 |

(a) The caesura value is .500
With RAT = ASAT/ALAT

SNIFF 4b2o, optimized, variant with different caesura so as to eliminate the Métavir F0 false positives, the β coefficients are unchanged.

| | | Predicted | | |
|---|---|---|---|---|
| | | F0 + 1 vs 2-4 | | Correct |
| Observed | | .00 | 1.00 | percentage |
| F0 + 1 vs 2-4 | .00 | 24 | 1 | 96.0 |
| | 1.00 | 4 | 59 | 93.7 |
| Overall percentage | | | | 94.3 |

The caesura value is .550

17. For SNIFFA 4c with 3 markers for fibrosis + age:

| | B | S.D. | Signif. | Exp (B) | CI for Exp (B) 95.0% | |
|---|---|---|---|---|---|---|
| | | | | | Lower | Upper |
| HA | .032 | .012 | .007 | 1.032 | 1.009 | 1.056 |
| A2M | .015 | .008 | .068 | 1.015 | .999 | 1.032 |

-continued

17. For SNIFFA 4c with 3 markers for fibrosis + age:

| | B | S.D. | Signif. | Exp (B) | Lower | Upper |
|---|---|---|---|---|---|---|
| AGE | −.140 | .058 | .015 | .869 | .776 | .973 |
| PT | −.169 | .067 | .012 | .845 | .741 | .963 |
| Constant | 16.541 | 7.858 | .035 | 15263638.220 | | |

| | | Predicted | | |
|---|---|---|---|---|
| | | F0 + 1 vs 2-4 | | Correct |
| Observed | | .00 | 1.00 | percentage |
| F0 + 1 vs 2-4 | .00 | 25 | 2 | 92.6 |
| | 1.00 | 5 | 56 | 91.8 |
| Overall percentage | | | | 92.0 |

Classification table. The caesura is at 0.50.

18. For SNIFFA 4co with 3 markers for fibrosis + age:

Classification table.

| | B | S.D. | Signif. | Exp (B) | CI for Exp (B) 95.0% | |
|---|---|---|---|---|---|---|
| | | | | | Lower | Upper |
| HA | .078 | .031 | .013 | 1.081 | 1.017 | 1.150 |
| A2M | .049 | .024 | .047 | 1.050 | 1.001 | 1.101 |
| AGE | −.550 | .219 | .011 | .571 | .372 | .878 |
| PT | −.629 | .266 | .018 | .533 | .316 | .898 |
| Constant | 68.252 | 29.471 | .021 | 43808673511370180000000000000000.0 | | |

18. For SNIFFA 4co with 3 markers for fibrosis + age:

| | Predicted | | Correct |
|---|---|---|---|
| | F0 + 1 vs 2-4 | | |
| Observed | .00 | 1.00 | percentage |
| F0 + 1 vs 24   .00 | 25 | 0 | 100.0 |
| 1.00 | 2 | 58 | 96.7 |
| Overall percentage | | | 97.6 |

The caesura is at 0.62.

19. For SNIDAFF 6a with 5 markers for fibrosis:

| | B | S.D. | Signif. | Exp (B) | CI for Exp (B) 95.0% | |
|---|---|---|---|---|---|---|
| | | | | | Lower | Upper |
| AGE | .031 | .012 | .008 | 1.032 | 1.008 | 1.056 |
| PLATELETS | −.006 | .002 | .002 | .994 | .990 | .998 |
| PT | −.076 | .015 | .000 | .927 | .900 | .956 |
| ASAT | .008 | .004 | .040 | 1.008 | 1.000 | 1.016 |
| ALP | .007 | .003 | .036 | 1.007 | 1.000 | 1.014 |
| A2M | .006 | .001 | .000 | 1.006 | 1.003 | 1.009 |
| Constant | 4.575 | 1.602 | .004 | 97.048 | | |

Classification table (a)

| | Predicted | | Correct |
|---|---|---|---|
| | F0 + 1 vs 2-4 | | |
| Observed | .00 | 1.00 | percentage |
| F0 + 1 vs 2-4   .00 | 114 | 40 | 74.0 |
| 1.00 | 34 | 189 | 84.8 |
| Overall percentage | | | 80.4 |

(a) The caesura value is .470

20. For SNIDAFF 6b with 5 markers for fibrosis:

| | B | S.D. | Signif. | Exp (B) | CI for Exp (B) 95.0% | |
|---|---|---|---|---|---|---|
| | | | | | Lower | Upper |
| AGE | .061 | .012 | .000 | 1.063 | 1.038 | 1.089 |
| PLATELETS | −.010 | .002 | .000 | .990 | .986 | .995 |
| PT | −.101 | .017 | .000 | .904 | .874 | .935 |
| ASAT | .017 | .004 | .000 | 1.017 | 1.008 | 1.026 |
| ALP | .015 | .004 | .000 | 1.015 | 1.007 | 1.023 |
| UREA | −.157 | .066 | .017 | .855 | .751 | .973 |
| Constant | 7.817 | 1.741 | .000 | 2483.002 | | |

Classification table (a)

| | Predicted | | Correct |
|---|---|---|---|
| | F0 + 1 vs 2-4 | | |
| Observed | .00 | 1.00 | percentage |
| F0 + 1 vs 2-4   .00 | 109 | 60 | 64.5 |
| 1.00 | 35 | 215 | 86.0 |
| Overall percentage | | | 77.3 |

(a) The caesura value is .400

21. For SNIAH:

Variables in the equation

| | | B | S.D. | Wald | ddl | Signif. | Exp (B) |
|---|---|---|---|---|---|---|---|
| Stage | ALAT | .010 | .002 | 22.575 | 1 | .000 | 1.010 |
| | Constant | −.474 | .200 | 5.601 | 1 | .018 | .622 |

Classification table (a)

| | | Predicted | | Correct |
|---|---|---|---|---|
| | | ACTIVICS | | |
| | Observed | .00 | 1.00 | percentage |
| Stage | ACTIVICS   .00 | 57 | 93 | 38.0 |
| | 1.00 | 33 | 193 | 85.4 |
| | Overall percentage | | | 66.5 |

(a) The caesura value is .500

22. For SNIAH o:

| | B | S.D. | Signif. | Exp (B) | CI for Exp (B) 95.0% | |
|---|---|---|---|---|---|---|
| | | | | | Lower | Upper |
| ALAT | .018 | .003 | .000 | 1.018 | 1.012 | 1.024 |
| Constant | −1.003 | .237 | .000 | .367 | | |

| | Predicted | | Correct |
|---|---|---|---|
| | ACTIVICS | | |
| Observed | .00 | 1.00 | percentage |
| ACTIVICS   .00 | 73 | 71 | 50.7 |
| 1.00 | 59 | 167 | 73.9 |
| Overall percentage | | | 64.9 | a The caesura value is .500

23. For SNIFFSA 3:

Variables in the equation

| | B | S.D. | Signif. | Exp (B) | CI for Exp (B) 95.0% | |
| --- | --- | --- | --- | --- | --- | --- |
| | | | | | Lower | Upper |
| PLATELETS | −.012 | .006 | .047 | .988 | .976 | 1.000 |
| PT | −.090 | .040 | .025 | .914 | .844 | .989 |
| NA | −.348 | .158 | .027 | .706 | .518 | .962 |
| Constant | 59.293 | 22.781 | .009 | 563129937938155000000000000.000 | | |

Classification table (a)

| | | Predicted | | Correct |
| --- | --- | --- | --- | --- |
| | | F < 2 vs >=2 | | |
| Observed | | .00 | 1.00 | percentage |
| F < 2 vs >=2 | .00 | 18 | 2 | 90.0 |
| | 1.00 | 1 | 20 | 95.2 |
| Overall percentage | | | | 92.7 |

(a) The caesura value is .500

24. For SNIFFSA 4a:

| | B | S.D. | Signif. | Exp (B) | CI for Exp (B) 95.0% | |
| --- | --- | --- | --- | --- | --- | --- |
| | | | | | Lower | Upper |
| PT | −.143 | .051 | .005 | .866 | .783 | .958 |
| AGE | .130 | .049 | .008 | 1.139 | 1.034 | 1.254 |
| GLYCEMIA | .566 | .333 | .089 | 1.761 | .917 | 3.383 |
| ASAT | .025 | .014 | .073 | 1.025 | .998 | 1.053 |
| Constant | 1.134 | 5.286 | .830 | 3.107 | | |

| | | Predicted | | Correct |
| --- | --- | --- | --- | --- |
| | | F < 2 vs >=2 | | |
| Observed | | .00 | 1.00 | percentage |
| F < 2 vs >=2 | .00 | 25 | 1 | 96.2 |
| | 1.00 | 4 | 25 | 86.2 |
| Overall percentage | | | | 90.9 |

The caesura value is .500

25. For SNIFFSA 4ao:

| | B | S.D. | Signif. | Exp (B) | CI for Exp (B) 95.0% | |
| --- | --- | --- | --- | --- | --- | --- |
| | | | | | Lower | Upper |
| PT | −.362 | .184 | .050 | .696 | .485 | .999 |
| AGE | .407 | .205 | .047 | 1.503 | 1.006 | 2.245 |
| GLYCEMIA | 1.424 | .962 | .139 | 4.154 | .630 | 27.384 |
| ASAT | .089 | .053 | .092 | 1.093 | .986 | 1.212 |
| Constant | −2.362 | 8.803 | .788 | .094 | | |

25. For SNIFFSA 4ao:

| | | Predicted | | Correct |
| --- | --- | --- | --- | --- |
| | | F < 2 vs >=2 | | |
| Observed | | .00 | 1.00 | percentage |
| F < 2 vs >=2 | .00 | 24 | 1 | 96.0 |
| | 1.00 | 1 | 27 | 96.4 |
| Overall percentage | | | | 96.2 | a The caesura value is .500

26. For SNIFFSA 4b:

| | B | S.D. | Signif. | Exp (B) | CI for Exp (B) 95.0% | |
| --- | --- | --- | --- | --- | --- | --- |
| | | | | | Lower | Upper |
| PT | −.105 | .047 | .026 | .900 | .821 | .987 |
| AGE | .140 | .057 | .014 | 1.150 | 1.029 | 1.286 |
| GLYCEMIA | .931 | .357 | .009 | 2.537 | 1.261 | 5.107 |
| TRI-GLYCERIDES | −1.889 | 1.023 | .065 | .151 | .020 | 1.122 |
| Constant | −1.697 | 5.243 | .746 | .183 | | |

| | | | Predicted | | Correct |
| --- | --- | --- | --- | --- | --- |
| | | | F < 2 vs >=2 | | |
| | Observed | | .00 | 1.00 | percentage |
| Stage 1 | F < 2 vs >=2 | .00 | 21 | 2 | 91.3 |
| | | 1.00 | 2 | 22 | 91.7 |
| Overall percentage | | | | | 91.5 | a The caesura value is .500

27. For SNIFFAV 5:

Variables in the equation

|  | B | S.D. | Signif. | Exp (B) | CI for Exp (B) 95.0% Lower | Upper |
|---|---|---|---|---|---|---|
| PLATELETS | −.008 | .002 | .000 | .992 | .988 | .997 |
| PT | −.051 | .017 | .002 | .950 | .920 | .982 |
| HA | .019 | .004 | .000 | 1.020 | 1.011 | 1.028 |
| A2M | .007 | .001 | .000 | 1.007 | 1.004 | 1.010 |
| UREA | −.199 | .065 | .002 | .819 | .721 | .931 |
| Constant | 4.648 | 1.665 | .005 | 104.330 | | |

Classification table (a)

|  |  |  | Predicted F0 + 1 vs 2-4 | | Correct |
|---|---|---|---|---|---|
| Observed | | | .00 | 1.00 | percentage |
| Stage | F0 + 1 vs 2-4 | .00 | 131 | 28 | 82.4 |
| | | 1.00 | 40 | 186 | 82.3 |
| Overall percentage | | | | | 82.3 |

(a) The caesura value is .500

28. For SNIFFAV 5o:

|  | B | S.D. | Signif. | Exp (B) | CI for Exp (B) 95.0% Lower | Upper |
|---|---|---|---|---|---|---|
| PLT | −.009 | .002 | .000 | .991 | .986 | .996 |
| PT | −.076 | .020 | .000 | .927 | .891 | .964 |
| UREA | −.314 | .083 | .000 | .731 | .621 | .861 |
| HA | .035 | .007 | .000 | 1.036 | 1.021 | 1.051 |
| A2M | .008 | .002 | .000 | 1.008 | 1.005 | 1.012 |
| Constant | 7.105 | 2.036 | .000 | 1218.006 | | |

Classification table

|  |  |  | Predicted F0 + 1 vs 2-4 | | Correct |
|---|---|---|---|---|---|
| Observed | | | .00 | 1.00 | percentage |
| F0 + 1 vs 2-4 | | .00 | 121 | 29 | 80.7 |
| | | 1.00 | 30 | 194 | 86.6 |
| Overall percentage | | | | | 84.2 |

The caesura value is .490

29. For SNIFFAV 6:

Variables in the equation

|  | B | S.D. | Signif. | Exp (B) | CI for Exp (B) 95.0% Lower | Upper |
|---|---|---|---|---|---|---|
| PLATELETS | −.008 | .002 | .000 | .992 | .988 | .996 |
| PT | −.052 | .016 | .002 | .950 | .920 | .981 |
| HA | .023 | .005 | .000 | 1.024 | 1.014 | 1.033 |
| A2M | .007 | .001 | .000 | 1.007 | 1.004 | 1.010 |
| CAUSE | 1.086 | .442 | .014 | 2.963 | 1.247 | 7.043 |
| UREA | −.271 | .073 | .000 | .762 | .660 | .880 |
| Constant | 3.124 | 1.752 | .075 | 22.737 | | |

29. For SNIFFAV 6:

Classification table (a)

|  |  |  | Predicted F0 + 1 vs 2-4 | | Correct |
|---|---|---|---|---|---|
| Observed | | | .00 | 1.00 | percentage |
| Stage | F0 + 1 vs 2-4 | .00 | 133 | 26 | 83.6 |
| | | 1.00 | 38 | 188 | 83.2 |
| Overall percentage | | | | | 83.4 |

(a) The caesura value is .500

30. For SNIFFAV 6o:

|  | B | S.D. | Signif. | Exp (B) | CI for Exp (B) 95.0% Lower | Upper |
|---|---|---|---|---|---|---|
| PLT | −.010 | .003 | .000 | .990 | .985 | .995 |
| PT | −.055 | .018 | .002 | .946 | .913 | .981 |
| UREA | −.396 | .090 | .000 | .673 | .564 | .803 |
| HA | .041 | .008 | .000 | 1.042 | 1.026 | 1.058 |
| A2M | .008 | .002 | .000 | 1.008 | 1.005 | 1.011 |
| ETIO | −1.648 | .517 | .001 | .192 | .070 | .530 |
| Constant | 5.974 | 1.925 | .002 | 392.931 | | |

|  |  | Predicted F0 + 1 vs 2-4 | | Correct |
|---|---|---|---|---|
| Observed | | .00 | 1.00 | percentage |
| F0 + 1 vs 2-4 | .00 | 123 | 29 | 80.9 |
| | 1.00 | 36 | 189 | 84.0 |
| Overall percentage | | | | 82.8 |

The caesura value is .500. As may be noted, the gain in effectiveness occurs not with respect to the diagnostic effectiveness (82.8 vs 83.5%), but with respect to other effectiveness indices, such as the area under the ROC curve (0.910 vs 0.890).

The SNIAFF, SNIAFFA, SNIAFFSA, SNIAFFAV and SNIDIFFAV scores were linear regression with the following procedure:

Firstly, the variables were tested in univariable analysis.

In a second step, the variables that were significant in univariable analysis were tested in multivariable analysis by linear regression with ascending step by step selection.

The linear statistical model is described by the following equation:

$$y_i = a + \beta_1 x_1 + \beta_2 x_2 +$$

where a is the constant, $\beta_i$ is the coefficient of each independent variable $x_i$, and $Y_i$ is the dependent variable (area of fibrosis).

We give below the tables for each score with, in the first column, the name of each independent variable, in the second column, the value of the coefficient $\beta$ and then its standard deviation, then the standardized coefficient $\beta$ and, in the last two columns, the confidence interval at 95% for the coefficient $\beta$.

For each score, as defined in the variants of the invention above, the overall predictive value of the model is reflected, in a second table, by the coefficient R-two adjusted for each model, which is the percentage variability of $y_i$ explained by the independent variables of the model.

For each score, in the applicable equation, the coefficient $\beta_i$ of each independent variable $x_i$ can vary from the value $\beta$ given in the table corresponding to said score ±3.3 standard deviations, a value also given in the table. Similarly, $a_0$ can vary from the value of the constant given in the table ±3.3 standard deviations.

31. For SNIAFF 5 with 5 markers for fibrosis:
Summary of the model

| Model | R | R-two | R-two adjusted | Standard error of the estimation |
|---|---|---|---|---|
| | .809 | .655 | .645 | 3.03260 |

With GAPRI = ((GGT/45)/PLT) × 100

32. For SNIAFF 6a:

| | Nonstandardized coefficients | | Standardized coefficients Beta | Significance | Confidence interval at 95% for B | |
|---|---|---|---|---|---|---|
| | B | Standard error | | | Lower limit | Upper limit |
| (constant) | 9.491 | 1.168 | | .000 | 7.186 | 11.797 |
| GAPRI | 3.037 | .317 | 1.033 | .000 | 2.411 | 3.664 |
| GGT | −.034 | .005 | −.652 | .000 | −.044 | −.024 |
| HA | .015 | .003 | .283 | .000 | .010 | .021 |
| APOA1 | −1.666 | .639 | −.122 | .010 | −2.927 | −.404 |
| BILI | .091 | .037 | .122 | .015 | .018 | .164 |

Summary of the model

| Model | R | R-two | R-two adjusted | Standard error of the estimation |
|---|---|---|---|---|
| | .798 | .637 | .625 | 3.13055 |

| | Nonstandardized coefficients | | Standardized coefficients Beta | Significance | Confidence interval at 95% for B | |
|---|---|---|---|---|---|---|
| | B | Standard error | | | Lower limit | Upper limit |
| (constant) | 6.739 | .885 | | .000 | 4.992 | 8.485 |
| HA | .017 | .003 | .297 | .000 | .011 | .022 |
| GAPRI | 2.945 | .327 | 1.130 | .000 | 2.301 | 3.590 |
| GGT | −.037 | .005 | −.842 | .000 | −.047 | −.027 |
| BILI | .106 | .037 | .139 | .005 | .033 | .180 |
| A2M | .005 | .002 | .116 | .020 | .001 | .010 |
| UREA | −.203 | .089 | −.107 | .024 | −.378 | −.027 |

With GAPRI = ((GGT/45)/PLT) × 100

33. For SNIAFF 6b:
Coefficients

| Model | R | R-two | R-two adjusted | Standard error of the estimation |
|---|---|---|---|---|
| | .802 | .643 | .631 | 3.10748 |

| | Nonstandardized coefficients | | Standardized coefficients Beta | Significance | Confidence interval at 95% for B | |
|---|---|---|---|---|---|---|
| | B | Standard error | | | Lower limit | Upper limit |
| (constant) | 6.014 | .981 | | .000 | 4.077 | 7.950 |
| HA | .016 | .003 | .286 | .000 | .010 | .022 |
| GAPRI | 2.844 | .327 | 1.094 | .000 | 2.199 | 3.489 |
| GGT | −.035 | .005 | −.803 | .000 | −.045 | −.025 |
| BILI | .111 | .037 | .145 | .003 | .038 | .185 |
| GGLOB | .156 | .053 | .145 | .004 | .051 | .261 |
| UREA | −.188 | .088 | −.100 | .033 | −.362 | −.015 |

With GAPRI = ((GGT/45)/PLT) × 100

34. For SNIAFFA 2:
Summary of the model

| R | R-two | R-two adjusted | Standard error of the estimation |
|---|---|---|---|
| .897 | .804 | .798 | 6.15243 |

Coefficients

| | Nonstandardized coefficients | | Standardized coefficients Beta | Significance | Confidence interval at 95% for B | |
|---|---|---|---|---|---|---|
| | B | Standard error | | | Lower limit | Upper limit |
| (constant) | 3.105 | 2.270 | | .176 | −1.420 | 7.631 |
| A2M | .019 | .008 | .130 | .019 | .003 | .035 |
| HA | .065 | .004 | .854 | .000 | .056 | .073 |

35. For SNIAFFA 3:
Summary of the model

| R | R-two | R-two adjusted | Standard error of the estimation |
|---|---|---|---|
| .902 | .814 | .806 | 6.03664 |

Coefficients

| | Nonstandardized coefficients | | Standardized coefficients Beta | Significance | Confidence interval at 95% for B | |
|---|---|---|---|---|---|---|
| | B | Standard error | | | Lower limit | Upper limit |
| HA | .062 | .004 | .824 | .000 | .054 | .071 |
| A2M | .020 | .008 | .134 | .014 | .004 | .035 |
| WEIGHT | .124 | .057 | .116 | .032 | .011 | .238 |

36. For SNIAFFA 4 with 3 markers for fibrosis:

| | Nonstandardized coefficients | | Standardized coefficients Beta | Significance | Confidence interval at 95% for B | |
|---|---|---|---|---|---|---|
| | B | Standard error | | | Lower limit | Upper limit |
| (constant) | −17.492 | 5.040 | | .001 | −27.554 | −7.429 |
| HYAMPRI | 4.242 | .504 | .605 | .000 | 3.235 | 5.249 |
| WEIGHT | .255 | .068 | .236 | .000 | .118 | .391 |
| PIIIP | 4.010 | 1.273 | .224 | .002 | 1.469 | 6.552 |
| A2M | .024 | .010 | .164 | .013 | .005 | .043 |

| Model | R | R-two | R-two adjusted | Standard error of the estimation |
|---|---|---|---|---|
| | .866 | .750 | .735 | 7.11277 | with HYAMPRI: (HA × A2M)/(A2M × 100)

37. For SNIAFFA 4o with 3 markers for fibrosis:

| | Nonstandardized coefficients | | Standardized coefficients-Beta | Significance | Confidence interval at 95% for B | |
|---|---|---|---|---|---|---|
| | B | Standard error | | | Lower limit | Upper limit |
| (constant) | −6.880 | 4.356 | | .119 | −15.590 | 1.831 |
| HYAMPRI | 5.470 | .478 | .752 | .000 | 4.515 | 6.426 |
| WEIGHT | .128 | .057 | .119 | .028 | .014 | .242 |
| A2M | .016 | .008 | .113 | .034 | .001 | .032 |
| PIIIP | 2.521 | 1.064 | .148 | .021 | .394 | 4.649 |

| Model | R | R-two | R-two adjusted | Standard error of the estimation |
|---|---|---|---|---|
| | .920 | .846 | .836 | 5.49377 |

38. For SNIAFFA 4a with 3 markers for fibrosis:

| | Nonstandardized coefficients | | Standardized coefficients Beta | Significance | Confidence interval at 95% for B | |
|---|---|---|---|---|---|---|
| | B | Standard error | | | Lower limit | Upper limit |
| (constant) | −10.122 | 4.720 | | .035 | −19.533 | −.711 |
| HYAMPRI | 4.285 | .473 | .624 | .000 | 3.341 | 5.228 |
| AMTRI | .022 | .005 | .285 | .000 | .011 | .033 |
| WEIGHT | .209 | .071 | .191 | .004 | .067 | .351 |

| Model | R | R-two | R-two adjusted | Standard error of the estimation |
|---|---|---|---|---|
| | .848 | .719 | .707 | 7.49622 | with HYAMPRI: (HA × A2M)/(A2M × 100), AMTRI: (A2M/PT) × 100

39. For SNIAFFA 4b with 3 markers for fibrosis:

| | Nonstandardized coefficients | | standardized coef-ficients Beta | Significance | Confidence interval at 95% for B | |
|---|---|---|---|---|---|---|
| | B | Standard error | | | Lower limit | Upper limit |
| (constant) | −10.670 | 4.637 | | .024 | −19.917 | −1.422 |
| HA | .042 | .005 | .613 | .000 | .032 | .051 |
| WEIGHT | .213 | .070 | .197 | .003 | .073 | .352 |
| AMTRI | .023 | .005 | .300 | .000 | .012 | .033 |

| Model | R | R-two | R-two adjusted | Standard error of the estimation |
|---|---|---|---|---|
| | .853 | .727 | .715 | 7.35058 | with AMTRI: (A2M/PT) × 100

40. For SNIAFFA 4co with 3 markers for fibrosis:

| | Nonstandardized coefficients | | standardized coef-ficients Beta | Significance | Confidence interval at 95% for B | |
|---|---|---|---|---|---|---|
| | B | Standard error | | | Lower limit | Upper limit |
| (constant) | 3.693 | 1.680 | | .032 | .337 | 7.049 |
| HAMPRI | −.700 | .314 | −.308 | .029 | −1.328 | −.073 |
| HYATRI | −.021 | .007 | −.551 | .003 | −.035 | −.007 |
| AMPRI | .026 | .010 | .227 | .009 | .007 | .045 |
| HYAMTRI | .517 | .158 | .398 | .002 | .201 | .832 |
| HYAMPRI | 8.853 | 1.293 | 1.243 | .000 | 6.269 | 11.437 |

| Model | R | R-two | R-two adjusted | Standard error of the estimation |
|---|---|---|---|---|
| | .922 | .849 | .837 | 5.50329 | with HAMPRI = (HA × A2M)/(PLT × 100), HYATRI: (HA/PT) × 100, AMPRI: (A2M/PLT) × 100, HYAMTRI: (HA × A2M)/(PT × 100), HYAMPRI: (HA × A2M)/(A2M × 100).

41. For SNIAFFAV 4:

| | Nonstandardized coefficients | | standardized coef-ficients Beta | Significance | Confidence interval at 95% for B | |
|---|---|---|---|---|---|---|
| | B | Standard error | | | Lower limit | Upper limit |
| (constant) | 20.659 | 4.496 | .413 | .000 | 11.805 | 29.513 |
| HA | .026 | .003 | | .000 | .020 | .033 |
| PT | −.180 | .041 | −.236 | .000 | −.261 | −.098 |
| BILI | .208 | .043 | .238 | .000 | .123 | .292 |
| A2M | .010 | .004 | .110 | .008 | .003 | .017 |

| Model | R | R-two | R-two adjusted | Standard error of the estimation |
|---|---|---|---|---|
| | .774 | .599 | .593 | 6.30666 |

42. For SNIAFFAV 5:

Summary of the model

| Model | R | R-two | R-two adjusted | Standard error of the estimation |
|---|---|---|---|---|
| | .880 | .775 | .770 | 3.95555 |

Coefficients

| | Nonstandardized coefficients | | standardized coef-ficients Beta | Significance | Confidence interval at 95% for B | |
|---|---|---|---|---|---|---|
| | B | Standard error | | | Lower limit | Upper limit |
| (constant) | 19.405 | 2.884 | | .000 | 13.724 | 25.085 |
| PLATELETS | −.006 | .003 | .059 | .077 | −.013 | .001 |
| PT | −.063 | .028 | −.094 | .025 | −.118 | −.008 |
| UREA | −.231 | .105 | −.073 | .028 | −.437 | −.025 |
| HA | .049 | .003 | .729 | .000 | .043 | .055 |
| Cause | −2.206 | .667 | −.119 | .001 | −3.520 | −.893 |

43. For SNIAFFAV 5b:

| | Nonstandardized coefficients | | standardized coef-ficients Beta | Significance | Confidence interval at 95% for B | |
|---|---|---|---|---|---|---|
| | B | Standard error | | | Lower limit | Upper limit |
| (constant) | 21.371 | 4.489 | | .000 | 12.530 | 30.212 |
| HA | .026 | .003 | .412 | .000 | .020 | .033 |
| PT | −.173 | .041 | −.227 | .000 | −.255 | −.092 |

43. For SNIAFFAV 5b:

| | | | | | |
|---|---|---|---|---|---|
| UREA | −.294 | .155 | −.077 | .060 | −.600 | .012 |
| BILI | .197 | .043 | .226 | .000 | .112 | .282 |
| A2M | .011 | .004 | .120 | .004 | .003 | .018 |

| Model | R | R-two | R-two adjusted | Standard error of the estimation |
|---|---|---|---|---|
| | .778 | .605 | .597 | 6.27506 |

44. For SNIAFFAV 5bo:

| | Nonstandardized coefficients | | standardized coefficients Beta | Significance | Confidence interval at 95% for B | |
|---|---|---|---|---|---|---|
| | B | Standard error | | | Lower limit | Upper limit |
| (constant) | 11.229 | 3.549 | | .002 | 4.238 | 18.220 |
| HA | .037 | .003 | .602 | .000 | .032 | .043 |
| PT | −.065 | .033 | −.095 | .049 | −.130 | .000 |
| UREA | −.264 | .118 | −.078 | .027 | −.497 | −.031 |
| BILI | .174 | .034 | .223 | .000 | .107 | .240 |
| A2M | .007 | .003 | .086 | .015 | .001 | .013 |

| Model | R | R-two | R-two adjusted | Standard error of the estimation |
|---|---|---|---|---|
| | .848 | .719 | .713 | 4.73071 |

45. For SNIAFFAV 5co:

| | Nonstandardized coefficients | | standardized coefficients Beta | Significance | Confidence interval at 95% for B | |
|---|---|---|---|---|---|---|
| | B | Standard error | | | Lower limit | Upper limit |
| (constant) | 9.300 | 1.387 | | .000 | 6.568 | 12.032 |
| HA | .032 | .004 | .496 | .000 | .024 | .041 |
| BILI | .126 | .031 | .164 | .000 | .065 | .187 |
| HYAMTRI | .313 | .073 | .255 | .000 | .169 | .457 |
| etio | −1.972 | .658 | −.104 | .003 | −3.268 | −.676 |

| Model | R | R-two | R-two adjusted | Standard error of the estimation |
|---|---|---|---|---|
| | .888 | .789 | .785 | 3.90275 | with HYAMTRI: (HA × A2M)/(PT × 100)

46. For SNIAFFAV 8:

| | Nonstandardized coefficients | | standardized coefficients Beta | Significance | Confidence interval at 95% for B | |
|---|---|---|---|---|---|---|
| | B | Standard error | | | Lower limit | Upper limit |
| (constant) | 1.443 | 1.211 | | .234 | −.941 | 3.828 |
| BILI | .166 | .039 | .192 | .000 | .089 | .243 |
| AMTRI | .035 | .007 | .531 | .000 | .020 | .049 |
| GLOPRI | .493 | .078 | .352 | .000 | .339 | .646 |
| HYAPRI | −.040 | .006 | −.653 | .000 | −.053 | −.028 |
| HA | .050 | .005 | .801 | .000 | .039 | .061 |
| A2M | −.029 | .009 | −.333 | .002 | −.047 | −.011 |
| GAPRI | .704 | .138 | .321 | .000 | .432 | .976 |
| APRI | −2.120 | .575 | −.231 | .000 | −3.252 | −.989 |

| Model | R | R-two | R-two adjusted | Standard error of the estimation |
|---|---|---|---|---|
| | .836 | .699 | .689 | 5.45747 | with AMTRI: (A2M/PT) × 100, GLOPRI: (GLB/PLT) × 100, HYAPRI: (HA/PLT) × 100, GAPRI = ((GGT/45)/PLT) × 100, APRI = (ASAT/PLT) × 100

47. For SNIDIFFAV 4a:

Summary of the model

| Model | R | R-two | R-two adjusted | Standard error of the estimation |
|---|---|---|---|---|
| | .826 | .682 | .660 | .11630 |

Coefficients

| | Nonstandardized coefficients | | standardized coefficients Beta | Significance | Confidence interval at 95% for B | |
|---|---|---|---|---|---|---|
| | B | Standard error | | | Lower limit | Upper limit |
| (constant) | 1.621 | .169 | | .000 | 1.283 | 1.959 |
| PT | −.003 | .002 | −.248 | .057 | −.006 | .000 |
| HA | .000 | .000 | .259 | .041 | .000 | .001 |
| A2M | .001 | .000 | .277 | .001 | .000 | .001 |
| ALB | −.011 | .003 | −.361 | .001 | −.017 | −.004 |

48. For SNIDIFFAV 4b

Coefficients

| | Nonstandardized coefficients | | standardized coefficients Beta | Significance | Confidence interval at 95% for B | |
|---|---|---|---|---|---|---|
| | B | Standard error | | | Lower limit | Upper limit |
| (constant) | 1.727 | .136 | | .000 | 1.455 | 1.999 |
| AGE | .002 | .001 | .155 | .061 | .000 | .005 |
| ALB | −.012 | .003 | −.397 | .000 | −.018 | −.006 |
| A2M | .001 | .000 | .266 | .001 | .000 | .001 |
| PT | −.004 | .001 | −.372 | .001 | −.007 | −.002 |

Summary of the model

| Model | R | R-two | R-two adjusted | Standard error of the estimation |
|---|---|---|---|---|
| | .827 | .684 | .662 | .11631 |

49. For SNIDIFFAV 6:

| | Nonstandardized coefficients | | standardized coefficients Beta | Significance | Confidence interval at 95% for B | |
|---|---|---|---|---|---|---|
| | B | Standard error | | | Lower limit | Upper limit |
| (constant) | 1.553 | .159 | | .000 | 1.235 | 1.870 |
| AGE | .003 | .001 | .176 | .031 | .000 | .005 |

-continued

49. For SNIDIFFAV 6:

| | | | | | |
|---|---|---|---|---|---|
| ALB | −.010 | .003 | −.336 | .002 | −.016 | −.004 |
| A2M | .001 | .000 | .267 | .001 | .000 | .001 |
| PT | −.004 | .001 | −.338 | .002 | −.007 | −.002 |
| RAT | .041 | .020 | .167 | .050 | .000 | .081 |

| Model | R | R-two | R-two adjusted | Standard error of the estimation |
|---|---|---|---|---|
| | .838 | .702 | .676 | .11340 |

50. For SNIAFFSA 4:

| | Nonstandardized coefficients | | standardized coefficients | Significance | Confidence interval at 95% for B | |
|---|---|---|---|---|---|---|
| | B | Standard error | Beta | | Lower limit | Upper limit |
| (constant) | 21.259 | 11.052 | | .065 | −1.418 | 43.937 |
| PT | −.249 | .089 | −.386 | .010 | −.432 | −.065 |
| AGE | .132 | .076 | .214 | .092 | −.023 | .288 |
| GGLOB | .987 | .308 | .455 | .003 | .355 | 1.618 |
| WEIGHT | −.073 | .042 | −.219 | .091 | −.159 | .012 |

| Model | R | R-two | R-two adjusted | Standard error of the estimation |
|---|---|---|---|---|
| | .780 | .608 | .550 | 5.36161 |

51. For SNIAFFSA 6:

| | Nonstandardized coefficients | | standardized coefficients | Significance | Confidence interval at 95% for B | |
|---|---|---|---|---|---|---|
| | B | Standard error | Beta | | Lower limit | Upper limit |
| (constant) | .501 | 3.705 | | .893 | −7.115 | 8.118 |
| WEIGHT | −.223 | .074 | −.685 | .006 | −.376 | −.071 |
| BMI | .551 | .240 | .520 | .030 | .059 | 1.044 |
| HYAPRI | −.150 | .044 | −1.421 | .002 | −.240 | −.061 |
| GLOPRI | 1.722 | .249 | .965 | .000 | 1.211 | 2.234 |
| HYATRI | .094 | .027 | 1.313 | .002 | .039 | .150 |

| Model | R | R-two | R-two adjusted | Standard error of the estimation |
|---|---|---|---|---|
| | .853 | .727 | .675 | 4.53214 |

52. For SNIAFFSA 6o:

| | Nonstandardized coefficients | | standardized coefficients | Significance | Confidence interval at 95% for B | |
|---|---|---|---|---|---|---|
| | B | Standard error | Beta | | Lower limit | Upper limit |
| (constant) | 1.774 | 2.805 | | .533 | −4.016 | 7.564 |
| WEIGHT | −.204 | .057 | −.725 | .002 | −.322 | −.086 |
| BMI | .489 | .184 | .537 | .014 | .109 | .869 |
| HYAPRI | −.086 | .036 | −.943 | .026 | −.162 | −.011 |
| GLOPRI | 1.578 | .193 | 1.029 | .000 | 1.180 | 1.976 |
| HYATRI | .049 | .023 | .784 | .041 | .002 | .097 |

| Model | R | R-two | R-two adjusted | Standard error of the estimation |
|---|---|---|---|---|
| | .898 | .806 | .766 | 3.40834 |

Other advantages and characteristics of the invention will emerge from the examples that follow, given by way of illustration, and in which reference will be made to the attached drawings, in which.

Figure 9:
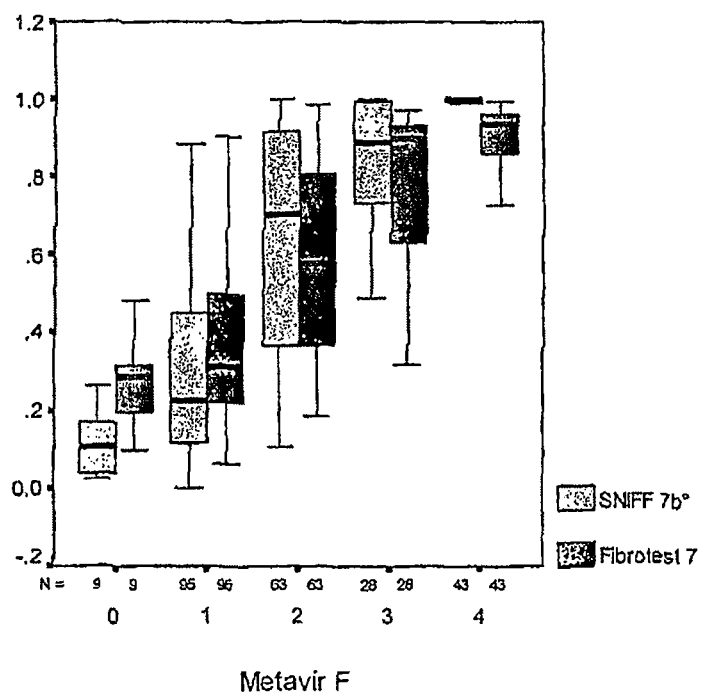

FIG. 9 shows a comparison of the Box plots for Fibrotest with 7 variables and for SNIFF 7bo with 7 variables in the same population of 238 patients with viral hepatitis. The Box plots for SNIFF 7bo are lower for the Métavir F0 and F1 stages and higher for the Métavir F2, F3 and F4 stages, than those of the Fibrotest 7, thus explaining the better discriminating ability of SNIFF 7bo for clinically significant fibrosis, which is determined with respect to the caesura value 0.50 for Fibrotest and 0.29 for SNIFF 7bo.

EXAMPLE 1

Determination of an SNIFF Score

A. Patients

The patient with chronic liver disease has a blood sample taken. The simple biological blood variables are determined according to good laboratory practice. The results are expressed with the units previously specified.

B. Assaying Methods

The hyaluronate concentration in a blood sample is measured by means of a radioimmunoassay technique (Kabi-Pharmacia RIA Diagnostics, Uppsala, Sweden).

The $A_2M$ concentration is determined by laser immunonephelometry using a Behring nephelometer analyzer. The reagent is a rabbit anti-human A2M antiserum.

The prothrombin time is measured from the Quick time (QT) which is determined by adding calcium thromboplastin (for example, Neoplastin CI plus, Diagnostica Stago, Asnières, France) to the plasma and the clotting time is measured in seconds. To obtain the prothrombin time (PT), a calibration line is plotted from various dilutions of a pool of normal plasmas estimated at 100%.

C. Calculation of the SNIFF Score

The results of the isolated (or simple) variables are used as they are or after conversion to combinatorial variables where appropriate. All these variables are included in the logistic regression formula. By way of example, and on the basis of the tables already described and of an example of formula use already described, those skilled in the art wishing to use the SNIFF 4a score with 4 markers will employ the following formula:

$$P=1/(1+\exp(-a_0-a_1(HA \text{ in } \mu g/l)-a_2(PT \text{ in }\%)-a_3(A2M \text{ in } mg/dl)=a_4(AGE \text{ in years})))$$

i.e.

$$p=1/(1+\exp(-2.365-(0.011\times(HA \text{ in } \mu g/l))-(-0.062\times(PT \text{ in }\%))-(0.006\times(A2M \text{ in } mg/dl))-(0.030\times(AGE \text{ in years}))))$$

Two opposite examples are given:

| Case | HA (µg/l) | PT (%) | A2M (mg/dl) | Age (years) | Probability |
|---|---|---|---|---|---|
| 1 | 273 | 90 | 374 | 64.0 | 0.981 |
| 5 | 25 | 89 | 157 | 30.2 | 0.273 |

Case 1 will be classified as having a clinically significant hepatic fibrosis and case 5 will be classified as not having any according to the caesura fixed at 0.50.

EXAMPLE 2

Figure 1:
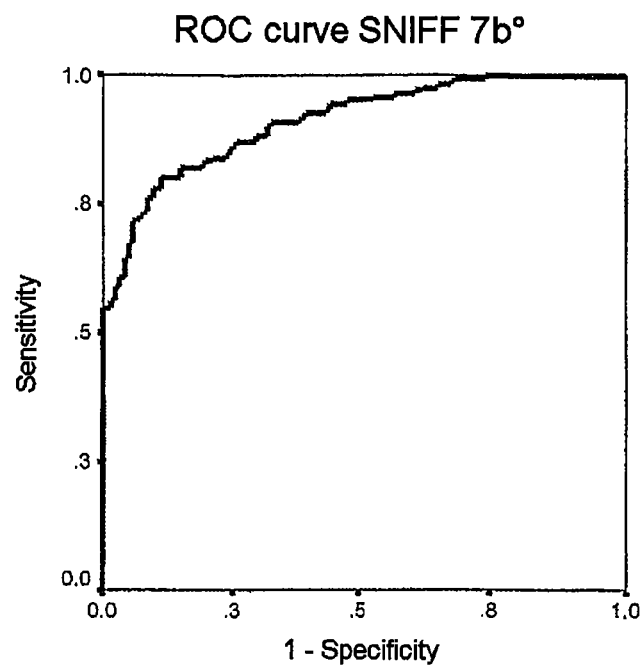
FIG. 1 shows the ROC curve obtained from the SNIFF 7bo score for clinically significant fibrosis. The statistical C (or area under the ROC curve) is 0.910±0.016.

Effectiveness of the Scores of the Invention and Comparison of the Results Obtained with the Scores of the Invention and the Methods of the Prior Art The ROC curve (FIG. 1) represents the specificity and the sensitivity as a function of the value of the test. It is measured by virtue of the index C which is considered to be clinically relevant from 0.7. The closer the curve is to the upper left corner of the box (specificity and sensitivity of 100%), the better it is. This is measured by the area under the ROC curve (AUROC), also called statistical C. It is possible to compare these AUROCs, hence an additional advantage that makes it possible to demonstrate the surprising effect of the SNIFF scores according to the invention (FIG. 8).

Figure 8:
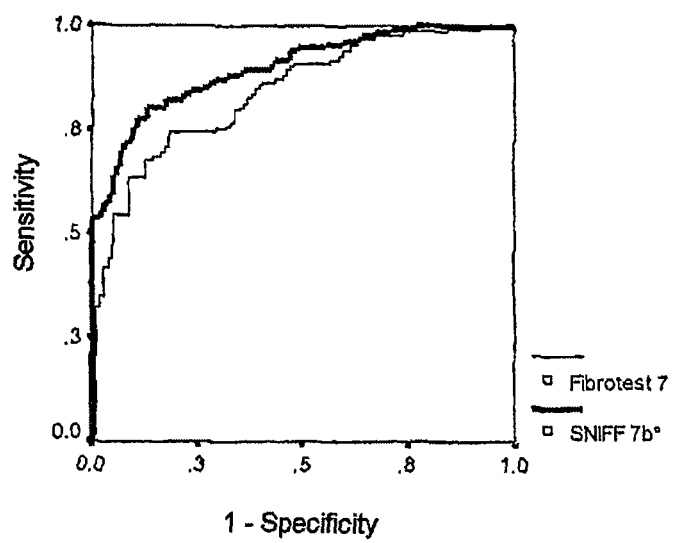
FIG. 8 shows a comparison of the ROC curves for Fibrotest 7 variables (C index: 0.839) and for SNIFF 7o with 7 variables (C index: 0.900) in the same population of 238 patients. The difference is statistically significant (p=0.0036 by the Hanley-McNeil method)

The index C obtained in the context of the tests of the invention has a value of 0.841±0.025 for the SNIFF 5 score and of 0.910±0.016 for the SNIFF 7bo score (FIG. 8). These indices C are therefore clinically relevant.

Figure 2:
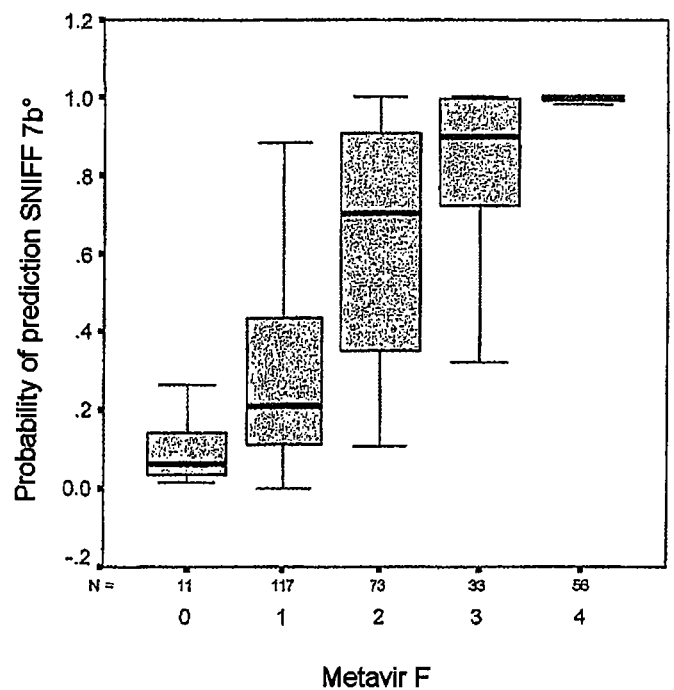
FIG. 2 is a representation of the Box plots (median, quartiles and extremes) of the SNIFF 7bo score with 7 variables versus the Métavir F score (the reference is measured by means of LNB)

The box plots presented in FIG. 2 show the statistical distribution of the SNIFF classes according to the Métavir F stages: medians (bold horizontal black line), quartiles (top and bottom limits of the gray rectangle) and extremes (horizontal bars at the extremities). The score involved is the SNIFF 7bo score.

Figure 3:
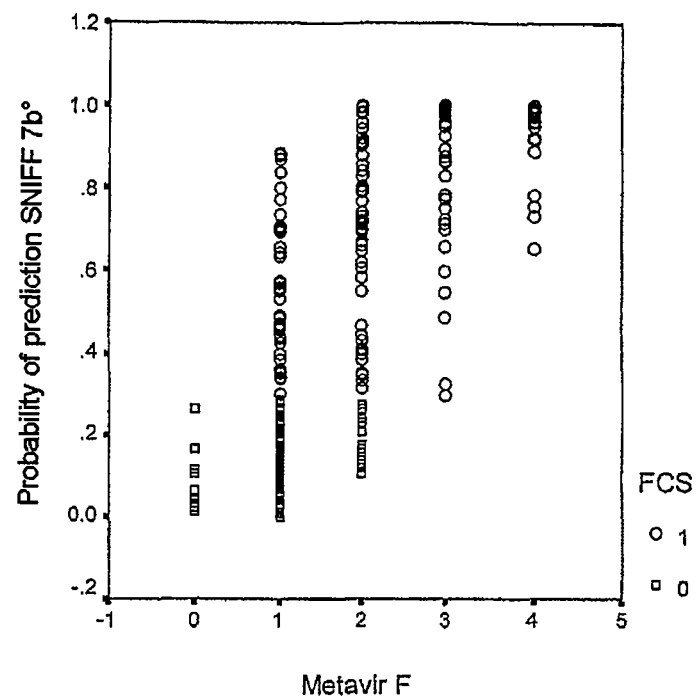
FIG. 3 shows the distribution of the SNIFF 7bo score with 7 variables versus the Métavir F score (the reference is measured by means of LNB)

FIG. 3 involves the same expression of the results as in FIG. 2, but it shows the individual raw data for SNIFF 7bo obtained using 7 variables as a function of the Métavir F score. The predicted groups: $\geq F2$: 0 (square): no, 1: yes (circle) are also shown (FIG. 3). This figure makes it possible to clearly see the overlaps in score, in particular between the Métavir F2 and F3 stages. On the other hand, in the numerous populations, it accounts poorly for the distribution due in particular to the superpositions of the individual values.

Figure 4:
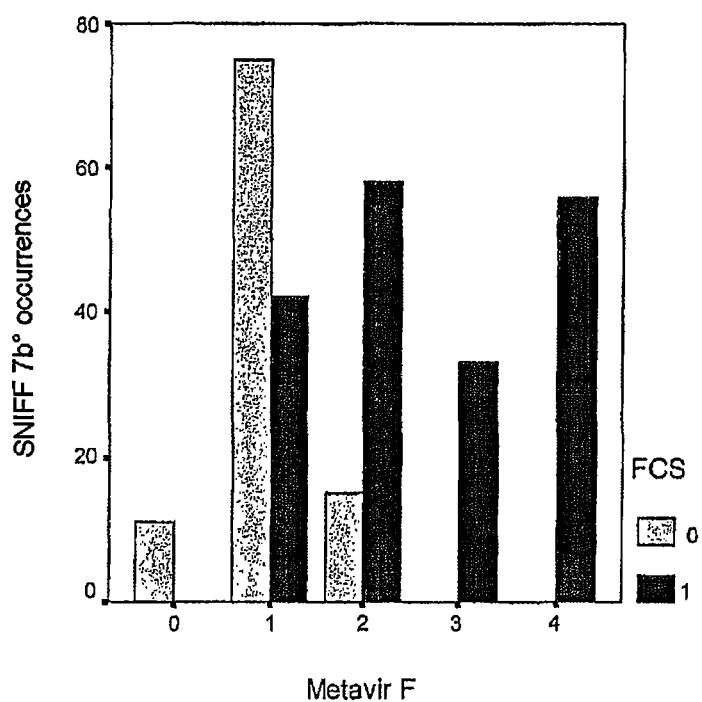
FIG. 4 shows the distribution of the predicted groups ($\geq$F2: 0: no, 1: yes) for the SNIFF 7bo score with 7 variables as a function of the Métavir F score.

FIG. 4 is a different expression of the previous figure (FIG. 3) in which the patients are grouped together by predicted group of clinically significant fibrosis predicted: $\geq F2$: 0 (gray): no, 1: yes (black). This corresponded to the squares and circles, respectively, of FIG. 3. SNIFF does not incorrectly classify any patient for F0 and F4 and very few for F3 (none in the case of SNIFF 7bo of FIG. 4). In other words, in practice, SNIFF 7bo correctly classifies 100% of the patients for the absence of fibrosis or the presence of cirrhosis.

Figure 5:
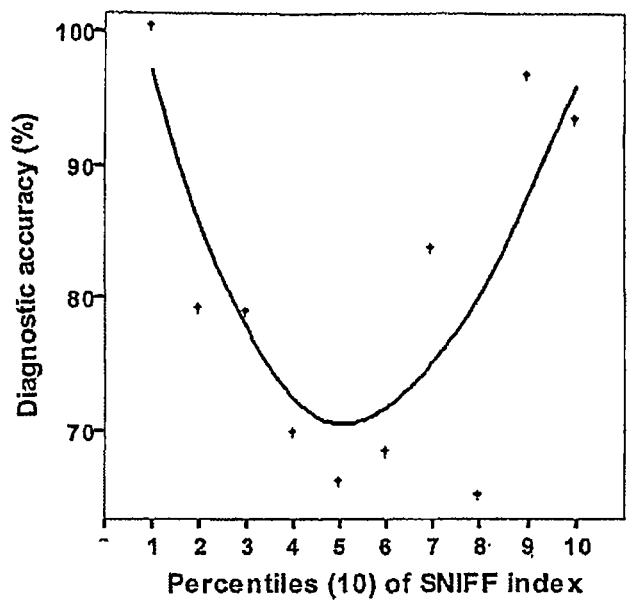
FIG. 5 shows the diagnostic effectiveness of the SNIFF 5 score as a function of its value.

As could be guessed on the previous figures, FIG. 5 makes it possible to clearly see that the diagnostic effectiveness is excellent for the low and high values and decreases for the middle values of the score. Thus, the diagnostic effectiveness is 90.8% for 50.0% of the patients with an SNIFF 5 score (FIG. 5).

The SNIFF 7 score with 7 variables gives a lower estimation of fibrosis: r=0.769, p<10$^{-4}$ than the SNIAFF 5o index with 5 variables: r=0.803, p<10$^{-4}$.

Figure 6:
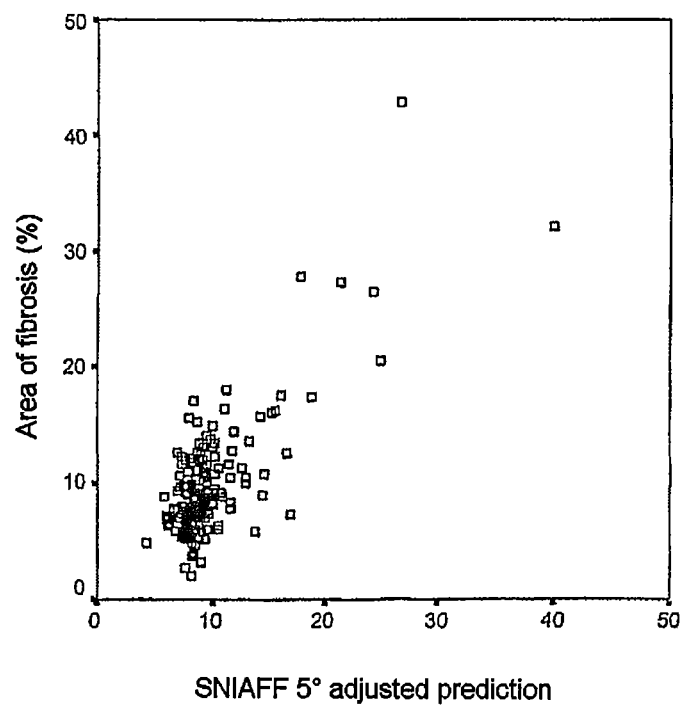
FIG. 6 shows the correlation between SNIAFF 5o with 5 variables and the area of fibrosis. This is to be compared with FIG. 3 (correlation between SNIFF 7bo with 7 variables and the F score) since these are the best indicators for viral liver pathologies.

This comparison shows that the SNIAFF estimate score for the area of fibrosis (FIG. 6) is a more reliable (accurate) indicator than the SNIFF score for fibrosis.

Similarly, the SNIFFA 4bo score with 4 variables gives a lower estimation of fibrosis: r=0.847, p<10$^{-4}$ than the SNIAFFA 4o index with 4 variables: r=0.914, p<10$^{-4}$.

Figure 7:
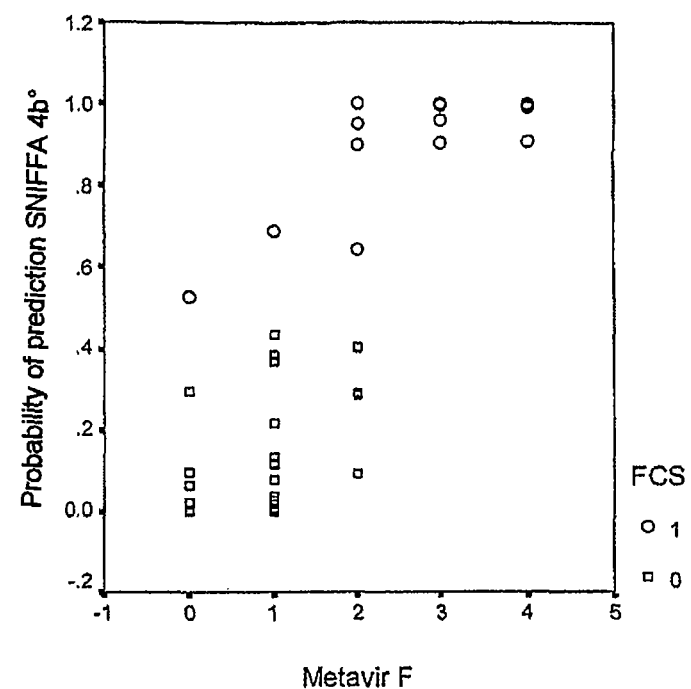
FIG. 7 shows the correlation between SNIFFA 4bo with 4 variables and the F score (FIG. 7A) and between SNIAFFA 4o with 4 variables and the area of fibrosis (FIG. 7B) (best indicators for alcoholic liver pathologies), FCS: clinically significant fibrosis.
Figure 7:
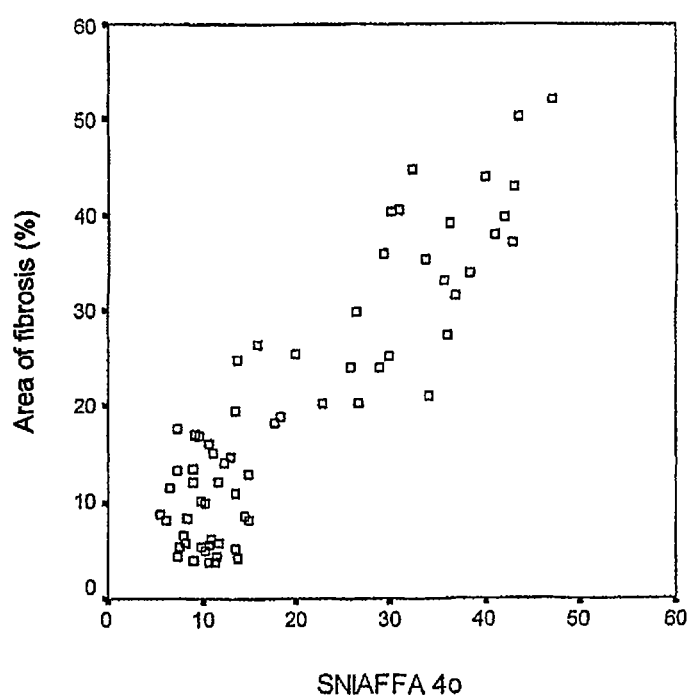

This comparison also shows that the SNIAFFA estimate score for the area of fibrosis is a more reliable (accurate) indicator than the SNIFFA score for fibrosis (FIG. 7) also in alcoholic liver pathologies.

The comparison of the SNIFF effectiveness and the Fibrotest effectiveness shows that the diagnostic effectiveness for Fibrotest 7 is 74.2% vs 82.1% for SNIFF 7. The AUROCs make it possible to show that the difference in effectiveness is statistically very significant (FIG. 8). FIG. 9 shows graphically the better discriminating ability of SNIFF 7 with respect to Fibrotest 7.

References

1. Oberti F, Valsesia E, Pilette C, Rousselet M, Bedossa P. Aubé C et al, Calès P. Noninvasive diagnosis of hepatic fibrosis or cirrhosis. Gastroenterology 1997; 113: 1609-16.

2. Croquet V, Vuillemin E, Ternisien C, Pilette C, Oberti F, Gallois Y, Trossaert M, Rousselet M C, Chappard D, Calès P. Prothrombin index is an indirect marker of severe liver fibrosis. Eur J Gastroenterol Hepatol 2002; 14: 1133-41.

3. Pilette C, Calès P. Existe-t-il des marqueurs sanguins de fibrose hépatique utilisables en pratique clinique? [Do blood markers for hepatic fibrosis, that can be used in clinical practice, exist?] Rev Med Interne 2002; 23: 885-8.

4. Pilette C, Rousselet M, Bedossa P, Chappard D, Oberti F, Rifflet H et al, Calès P. Histopathological evaluation of liver fibrosis: quantitative image analysis vs semi-quantitative scores: comparison with serum markers. J Hepatol 1998; 28: 439-46.

5. Aubé C, Oberti F, Korali N, Korali N, Namour A, L et al, Calès P. Ultrasonographic diagnosis of hepatic fibrosis or cirrhosis. J Hepatol 1999; 30: 472-8.

6. Moal F, Chappard D, Wang J, Vuillemin E, Michalak-Provost S, Rousselet M C, Oberti F, Calès P. Fractal dimension can distinguish models and pharmacological changes in liver fibrosis in rats. Hepatology 2002; 36: 840-9.

7. Michalak S, Rousselet M C, Bedossa P, Pilette C, Chappard D, Oberti F, Gallois Y, Calès P. Respective role of portoseptal fibrosis and centrolobular fibrosis in alcoholic liver diseases. J Pathol 2003; 201: 55-62.

What is claimed is:

1. A method of diagnosing a presence and/or severity of a liver pathology in an individual, comprising establishing at least one non-invasive diagnostic score, by carrying out the following steps:
   a) measuring, in a sample from said individual six variables, wherein one of said six variables is α-2 macroglobulin (A2M) and five of said six variables are chosen from the group consisting of hyaluronic acid (HA or hyaluronate), gamma-glutamyltranspeptidase (GGT), platelets (PLT), prothrombin time (PT), aspartate aminotransferase (ASAT), and urea;
   b) collecting at least one clinical variable characterizing said individual;
   c) combining said six variables from steps a) and at least one clinical variable b) in a logistic or linear function, in order to obtain a diagnostic score; and
   d) diagnosing the presence and/or severity of said pathology based on the score obtained from step (c),
   wherein said diagnostic score gives a percentage of correct classification of at least 79.4%.

2. The method as claimed in claim 1, characterized in that the at least one clinical variable characterizing the individual is chosen from body weight, body mass index, age at the date on which the sample was collected, and cause.

3. The method as claimed in claim 1, characterized in that, prior to step (c), the variables measured in step (a) and the at least one variable collected in step (b) are combined with one another.

4. The method as claimed in claim 1, characterized in that said liver pathology is chosen from liver diseases of viral origin, liver diseases of alcoholic origin and steatosis.

5. The method as claimed in claim 1, characterized in that the variables α-2 macroglobulin (A2M) and prothrombin time (PT), platelets (PLT), aspartate aminotransferase (ASAT), urea, and hyaluronic acid (HA) are measured in step (a) of said method.

6. The method as claimed in claim 5, characterized in that the following are combined in step (c):
   α-2 macroglobulin (A2M), prothrombin time (PT), platelets (PLT), aspartate aminotransferase (ASAT), urea, hyaluronic acid (HA) and age.

7. A diagnostic test for hepatic fibrosis, characterized in that it uses a method as claimed in claim 1.

8. The method as claimed in claim 1, characterized in that the liver pathology is liver fibrosis.

9. The method as claimed in claim 8, characterized in that the liver fibrosis is a portal and septal fibrosis.

10. The method as claimed in claim 1, characterized in that the variables α-2 macroglobulin (A2M) and prothrombin time (PT), platelets (PLT), aspartate aminotransferase (ASAT), urea, and gamma-glutamyltranspeptidase (GGT) are measured in step (a).

11. The method as claimed in claim 5, characterized in that the following are combined in step (c):α-2 macroglobulin (A2M), prothrombin time (PT), platelets (PLT), aspartate aminotransferase (ASAT), urea, gamma-glutamyltranspeptidase (GGT) and age.

* * * * *

UNITED STATES PATENT AND TRADEMARK OFFICE
CERTIFICATE OF CORRECTION

PATENT NO. : 8,489,335 B2  Page 1 of 1
APPLICATION NO. : 11/596486
DATED : July 16, 2013
INVENTOR(S) : Paul Cales It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1774 days.

Signed and Sealed this
Eighth Day of September, 2015

Michelle K. Lee
*Director of the United States Patent and Trademark Office*